US009959940B2

(12) United States Patent
Moffitt et al.

(10) Patent No.: US 9,959,940 B2
(45) Date of Patent: *May 1, 2018

(54) SYSTEMS AND METHODS FOR VOA MODEL GENERATION AND USE

(71) Applicant: Boston Scientific Neuromodulation Corporation, Valencia, CA (US)

(72) Inventors: Michael A. Moffitt, Saugus, CA (US); G. Karl Steinke, Valencia, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 0 days. days.

This patent is subject to a terminal disclaimer.

(21) Appl. No.: 15/456,351

(22) Filed: Mar. 10, 2017

(65) Prior Publication Data

US 2017/0185741 A1   Jun. 29, 2017

Related U.S. Application Data

(63) Continuation of application No. 13/973,113, filed on Aug. 22, 2013.

(Continued)

(51) Int. Cl.
*G06F 19/00* (2011.01)
*G06N 3/08* (2006.01)
(Continued)

(52) U.S. Cl.
CPC ......... *G16H 50/50* (2018.01); *A61N 1/36128* (2013.01); *A61N 1/37247* (2013.01);
(Continued)

(58) Field of Classification Search
CPC .......... G06N 5/04; G06N 5/02; G06N 99/005; G09B 7/04; G06F 9/4446
See application file for complete search history.

(56) References Cited

U.S. PATENT DOCUMENTS 3,999,555 A   12/1976 Person
4,144,889 A   3/1979 Tyers et al.
(Continued)

FOREIGN PATENT DOCUMENTS

EP   1048320   11/2000
EP   1166819   1/2002
(Continued)

OTHER PUBLICATIONS

"Development of Accurate Computational Models for Patient-Specific Deep Brain Stimulation" Ashutosh Chaturvedi; Department of Biomedical Engineering Case Western Reserve University Jan. 2012.*

(Continued)

*Primary Examiner* — Luis Sitiriche
(74) *Attorney, Agent, or Firm* — Lowe Graham Jones PLLC; Bruce E. Black

(57) ABSTRACT

A computer implemented system and method provides a volume of activation (VOA) estimation model that receives as input two or more electric field values of a same or different data type at respective two or more positions of a neural element and determines based on such input an activation status of the neural element. A computer implemented system and method provides a machine learning system that automatically generates a computationally inexpensive VOA estimation model based on output of a computationally expensive system.

20 Claims, 4 Drawing Sheets

Related U.S. Application Data

(60) Provisional application No. 61/721,112, filed on Nov. 1, 2012.

(51) Int. Cl.
*A61N 1/36* (2006.01)
*A61N 1/372* (2006.01)

(52) U.S. Cl.
CPC ........ *G06F 19/345* (2013.01); *G06F 19/3437* (2013.01); *G06N 3/084* (2013.01); *G06N 3/086* (2013.01); *G16H 50/20* (2018.01)

(56) References Cited

U.S. PATENT DOCUMENTS

| | | | |
|---|---|---|---|
| 4,177,818 A | 12/1979 | De Pedro |
| 4,378,797 A | 4/1983 | Osterholm |
| 4,445,500 A | 5/1984 | Osterholm |
| 4,735,208 A | 4/1988 | Wyler et al. |
| 4,765,341 A | 8/1988 | Mower et al. |
| 4,841,973 A | 6/1989 | Stecker |
| 5,067,495 A | 11/1991 | Brehm |
| 5,099,846 A | 3/1992 | Hardy |
| 5,222,494 A | 6/1993 | Baker, Jr. |
| 5,255,693 A | 10/1993 | Dutcher |
| 5,259,387 A | 11/1993 | dePinto |
| 5,304,206 A | 4/1994 | Baker, Jr. et al. |
| 5,361,763 A | 11/1994 | Kao et al. |
| 5,452,407 A | 9/1995 | Crook |
| 5,565,949 A | 10/1996 | Kasha, Jr. |
| 5,593,427 A | 1/1997 | Gliner et al. |
| 5,601,612 A | 2/1997 | Gliner et al. |
| 5,607,454 A | 3/1997 | Cameron et al. |
| 5,620,470 A | 4/1997 | Gliner et al. |
| 5,651,767 A | 7/1997 | Schulmann |
| 5,711,316 A | 1/1998 | Elsberry et al. |
| 5,713,922 A | 2/1998 | King |
| 5,716,377 A | 2/1998 | Rise et al. |
| 5,724,985 A | 3/1998 | Snell et al. |
| 5,749,904 A | 5/1998 | Gliner et al. |
| 5,749,905 A | 5/1998 | Gliner et al. |
| 5,776,170 A | 7/1998 | MacDonald et al. |
| 5,782,762 A | 7/1998 | Snell et al. |
| 5,843,148 A | 12/1998 | Gijsbers et al. |
| 5,859,922 A | 1/1999 | Hoffmann |
| 5,868,740 A | 2/1999 | LeVeen et al. |
| 5,897,583 A | 4/1999 | Meyer et al. |
| 5,910,804 A | 6/1999 | Fortenbery et al. |
| 5,925,070 A | 7/1999 | King et al. |
| 5,938,688 A | 8/1999 | Schiff |
| 5,938,690 A | 8/1999 | Law et al. |
| 5,978,713 A | 11/1999 | Prutchi et al. |
| 6,016,449 A | 1/2000 | Fischell et al. |
| 6,029,090 A | 2/2000 | Herbst |
| 6,029,091 A | 2/2000 | de la Rama et al. |
| 6,050,992 A | 4/2000 | Nichols |
| 6,058,331 A | 5/2000 | King |
| 6,066,163 A | 5/2000 | John |
| 6,083,162 A | 7/2000 | Vining |
| 6,094,598 A | 7/2000 | Elsberry et al. |
| 6,096,756 A | 8/2000 | Crain et al. |
| 6,106,460 A | 8/2000 | Panescu et al. |
| 6,109,269 A | 8/2000 | Rise et al. |
| 6,128,538 A | 10/2000 | Fischell et al. |
| 6,129,685 A | 10/2000 | Howard, III |
| 6,161,044 A | 12/2000 | Silverstone |
| 6,167,311 A | 12/2000 | Rezai |
| 6,181,969 B1 | 1/2001 | Gord |
| 6,192,266 B1 | 2/2001 | Dupree et al. |
| 6,205,361 B1 | 3/2001 | Kuzma |
| 6,208,881 B1 | 3/2001 | Champeau |
| 6,240,308 B1 | 5/2001 | Hardy et al. |
| 6,246,912 B1 | 6/2001 | Sluijter et al. |
| 6,253,109 B1 | 6/2001 | Gielen |
| 6,289,239 B1 | 9/2001 | Panescu et al. |
| 6,310,619 B1 | 10/2001 | Rice |
| 6,319,241 B1 | 11/2001 | King |
| 6,336,899 B1 | 1/2002 | Yamazaki |
| 6,351,675 B1 | 2/2002 | Tholen et al. |
| 6,353,762 B1 | 3/2002 | Baudino et al. |
| 6,366,813 B1 | 4/2002 | Dilorenzo |
| 6,368,331 B1 | 4/2002 | Front et al. |
| 6,389,311 B1 | 5/2002 | Whayne et al. |
| 6,393,325 B1 | 5/2002 | Mann et al. |
| 6,435,878 B1 | 8/2002 | Reynolds et al. |
| 6,442,432 B2 | 8/2002 | Lee |
| 6,463,328 B1 | 10/2002 | John |
| 6,491,699 B1 | 12/2002 | Henderson et al. |
| 6,494,831 B1 | 12/2002 | Koritzinsky |
| 6,507,759 B1 | 1/2003 | Prutchi et al. |
| 6,510,347 B2 | 1/2003 | Borkan |
| 6,516,227 B1 | 2/2003 | Meadows et al. |
| 6,517,480 B1 | 2/2003 | Krass |
| 6,539,263 B1 | 3/2003 | Schiff et al. |
| 6,579,280 B1 | 6/2003 | Kovach et al. |
| 6,600,956 B2 | 7/2003 | Maschino et al. |
| 6,606,523 B1 | 8/2003 | Jenkins |
| 6,609,029 B1 | 8/2003 | Mann et al. |
| 6,609,031 B1 | 8/2003 | Law et al. |
| 6,609,032 B1 | 8/2003 | Woods et al. |
| 6,622,048 B1 | 9/2003 | Mann et al. |
| 6,631,297 B1 | 10/2003 | Mo |
| 6,654,642 B2 | 11/2003 | North et al. |
| 6,662,053 B2 | 12/2003 | Borkan |
| 6,684,106 B2 | 1/2004 | Herbst |
| 6,687,392 B1 | 2/2004 | Touzawa et al. |
| 6,690,972 B2 | 2/2004 | Conley et al. |
| 6,690,974 B2 | 2/2004 | Archer et al. |
| 6,692,315 B1 | 2/2004 | Soumillion et al. |
| 6,694,162 B2 | 2/2004 | Hartlep |
| 6,694,163 B1 | 2/2004 | Vining |
| 6,708,096 B1 | 3/2004 | Frei et al. |
| 6,741,892 B1 | 5/2004 | Meadows et al. |
| 6,748,098 B1 | 6/2004 | Rosenfeld |
| 6,748,276 B1 | 6/2004 | Daignault, Jr. et al. |
| 6,778,846 B1 | 8/2004 | Martinez et al. |
| 6,788,969 B2 | 9/2004 | Dupree et al. |
| 6,795,737 B2 | 9/2004 | Gielen et al. |
| 6,827,681 B2 | 12/2004 | Tanner et al. |
| 6,830,544 B2 | 12/2004 | Tanner |
| 6,845,267 B2 | 1/2005 | Harrison et al. |
| 6,850,802 B2 | 2/2005 | Holsheimer |
| 6,895,280 B2 | 5/2005 | Meadows et al. |
| 6,909,913 B2 | 6/2005 | Vining |
| 6,937,891 B2 | 8/2005 | Leinders et al. |
| 6,937,903 B2 | 8/2005 | Schuler et al. |
| 6,944,497 B2 | 9/2005 | Stypulkowski |
| 6,944,501 B1 | 9/2005 | Pless |
| 6,950,707 B2 | 9/2005 | Whitehurst |
| 6,969,388 B2 | 11/2005 | Goldman et al. |
| 7,003,349 B1 | 2/2006 | Andersson et al. |
| 7,003,352 B1 | 2/2006 | Whitehurst |
| 7,008,370 B2 | 3/2006 | Tanner et al. |
| 7,008,413 B2 | 3/2006 | Kovach et al. |
| 7,035,690 B2 | 4/2006 | Goetz |
| 7,043,293 B1 | 5/2006 | Baura |
| 7,047,082 B1 | 5/2006 | Schrom et al. |
| 7,047,084 B2 | 5/2006 | Erickson et al. |
| 7,050,857 B2 | 5/2006 | Samuelsson et al. |
| 7,054,692 B1 | 5/2006 | Whitehurst et al. |
| 7,058,446 B2 | 6/2006 | Schuler et al. |
| 7,082,333 B1 | 7/2006 | Bauhahn et al. |
| 7,107,102 B2 | 9/2006 | Daignault, Jr. et al. |
| 7,126,000 B2 | 10/2006 | Ogawa et al. |
| 7,127,297 B2 | 10/2006 | Law et al. |
| 7,136,518 B2 | 11/2006 | Griffin et al. |
| 7,136,695 B2 | 11/2006 | Pless et al. |
| 7,142,923 B2 | 11/2006 | North et al. |
| 7,146,219 B2 | 12/2006 | Sieracki et al. |
| 7,146,223 B1 | 12/2006 | King |
| 7,151,961 B1 | 12/2006 | Whitehurst |
| 7,155,279 B2 | 12/2006 | Whitehurst |
| 7,167,760 B2 | 1/2007 | Dawant et al. |
| 7,177,674 B2 | 2/2007 | Echauz et al. |

(56) References Cited

U.S. PATENT DOCUMENTS

| | | |
|---|---|---|
| 7,181,286 B2 | 2/2007 | Sieracki et al. |
| 7,184,837 B2 | 2/2007 | Goetz |
| 7,191,014 B2 | 3/2007 | Kobayashi et al. |
| 7,209,787 B2 | 4/2007 | Dilorenzo |
| 7,211,050 B1 | 5/2007 | Caplygin |
| 7,216,000 B2 | 5/2007 | Sieracki et al. |
| 7,217,276 B2 | 5/2007 | Henderson |
| 7,218,968 B2 | 5/2007 | Condie et al. |
| 7,228,179 B2 | 6/2007 | Campen et al. |
| 7,231,254 B2 | 6/2007 | Dilorenzo |
| 7,236,830 B2 | 6/2007 | Gliner |
| 7,239,910 B2 | 7/2007 | Tanner |
| 7,239,916 B2 | 7/2007 | Thompson et al. |
| 7,239,926 B2 | 7/2007 | Goetz |
| 7,242,984 B2 | 7/2007 | DiLorenzo |
| 7,244,150 B1 | 7/2007 | Brase et al. |
| 7,252,090 B2 | 8/2007 | Goetz |
| 7,254,445 B2 | 8/2007 | Law et al. |
| 7,254,446 B1 | 8/2007 | Erickson |
| 7,257,447 B2 | 8/2007 | Cates et al. |
| 7,266,412 B2 | 9/2007 | Stypulkowski |
| 7,294,107 B2 | 11/2007 | Simon et al. |
| 7,295,876 B1 | 11/2007 | Erickson |
| 7,299,096 B2 | 11/2007 | Balzer et al. |
| 7,308,302 B1 | 12/2007 | Schuler et al. |
| 7,313,430 B2 | 12/2007 | Urquhart |
| 7,324,851 B1 | 1/2008 | Dilorenzo |
| 7,346,382 B2 | 3/2008 | Mcintyre et al. |
| 7,388,974 B2 | 6/2008 | Yanagita |
| 7,437,193 B2 | 10/2008 | Parramon et al. |
| 7,463,928 B2 | 12/2008 | Lee et al. |
| 7,499,048 B2 | 3/2009 | Sieracki et al. |
| 7,505,815 B2 | 3/2009 | Lee et al. |
| 7,548,786 B2 | 6/2009 | Lee et al. |
| 7,565,199 B2 | 7/2009 | Sheffield et al. |
| 7,603,177 B2 | 10/2009 | Sieracki et al. |
| 7,617,002 B2 | 11/2009 | Goetz |
| 7,623,918 B2 | 11/2009 | Goetz |
| 7,650,184 B2 | 1/2010 | Walter |
| 7,657,319 B2 | 2/2010 | Goetz et al. |
| 7,672,734 B2 | 3/2010 | Anderson et al. |
| 7,676,273 B2 | 3/2010 | Goetz et al. |
| 7,680,526 B2 | 3/2010 | McIntyre et al. |
| 7,734,340 B2 | 6/2010 | De Ridder |
| 7,761,165 B1 | 7/2010 | He et al. |
| 7,826,902 B2 | 11/2010 | Stone et al. |
| 7,848,802 B2 | 12/2010 | Goetz et al. |
| 7,860,548 B2 | 12/2010 | McIntyre et al. |
| 7,904,134 B2 | 3/2011 | McIntyre et al. |
| 7,945,105 B1 | 5/2011 | Jaenisch |
| 7,949,395 B2 | 5/2011 | Kuzma |
| 7,974,706 B2 | 7/2011 | Moffitt et al. |
| 8,019,439 B2 | 9/2011 | Kuzma et al. |
| 8,175,710 B2 | 5/2012 | He |
| 8,180,601 B2 | 5/2012 | Butson et al. |
| 8,195,300 B2 | 6/2012 | Gliner et al. |
| 8,224,450 B2 | 7/2012 | Brase |
| 8,257,684 B2 | 9/2012 | Covalin et al. |
| 8,262,714 B2 | 9/2012 | Hulvershom et al. |
| 8,364,278 B2 | 1/2013 | Pianca et al. |
| 8,429,174 B2 | 4/2013 | Ramani et al. |
| 8,452,415 B2 | 5/2013 | Goetz et al. |
| 8,543,189 B2 | 9/2013 | Paitel et al. |
| 8,606,360 B2 | 12/2013 | Butson et al. |
| 8,620,452 B2 | 12/2013 | King et al. |
| 8,831,731 B2 | 9/2014 | Blum et al. |
| 8,918,184 B1 | 12/2014 | Torgerson et al. |
| 2001/0031071 A1 | 10/2001 | Nichols et al. |
| 2002/0032375 A1 | 3/2002 | Bauch et al. |
| 2002/0099295 A1 | 7/2002 | Gil et al. |
| 2002/0115603 A1 | 8/2002 | Whitehouse |
| 2002/0116030 A1 | 8/2002 | Rezai |
| 2002/0151939 A1 | 10/2002 | Rezai |
| 2002/0183607 A1 | 12/2002 | Bauch et al. |
| 2002/0183740 A1 | 12/2002 | Edwards et al. |
| 2002/0183817 A1 | 12/2002 | Van Venrooij et al. |
| 2003/0097159 A1 | 5/2003 | Schiff et al. |
| 2003/0149450 A1 | 8/2003 | Mayberg |
| 2003/0171791 A1 | 9/2003 | KenKnight et al. |
| 2003/0212439 A1 | 11/2003 | Schuler et al. |
| 2004/0034394 A1 | 2/2004 | Woods et al. |
| 2004/0044279 A1 | 3/2004 | Lewin et al. |
| 2004/0054297 A1 | 3/2004 | Wingeier et al. |
| 2004/0059395 A1 | 3/2004 | North et al. |
| 2004/0106916 A1 | 6/2004 | Quaid et al. |
| 2004/0133248 A1 | 7/2004 | Frei et al. |
| 2004/0152957 A1 | 8/2004 | Stivoric et al. |
| 2004/0181262 A1 | 9/2004 | Bauhahn |
| 2004/0186532 A1 | 9/2004 | Tadlock |
| 2004/0199216 A1 | 10/2004 | Lee et al. |
| 2004/0267330 A1 | 12/2004 | Lee et al. |
| 2005/0021090 A1 | 1/2005 | Schuler et al. |
| 2005/0049649 A1 | 3/2005 | Luders et al. |
| 2005/0060001 A1 | 3/2005 | Singhal et al. |
| 2005/0060009 A1 | 3/2005 | Goetz |
| 2005/0070781 A1 | 3/2005 | Dawant et al. |
| 2005/0075689 A1 | 4/2005 | Toy et al. |
| 2005/0165294 A1 | 7/2005 | Weiss |
| 2005/0171587 A1 | 8/2005 | Daglow et al. |
| 2005/0228250 A1 | 10/2005 | Bitter et al. |
| 2005/0251061 A1 | 11/2005 | Schuler et al. |
| 2005/0261061 A1 | 11/2005 | Nguyen et al. |
| 2005/0261601 A1 | 11/2005 | Schuler et al. |
| 2005/0261747 A1 | 11/2005 | Schuler et al. |
| 2005/0288732 A1 | 12/2005 | Schuler et al. |
| 2006/0004422 A1 | 1/2006 | De Ridder |
| 2006/0017749 A1 | 1/2006 | Mcintyre et al. |
| 2006/0020292 A1 | 1/2006 | Goetz et al. |
| 2006/0069415 A1 | 3/2006 | Cameron et al. |
| 2006/0094951 A1 | 5/2006 | Dean et al. |
| 2006/0095088 A1 | 5/2006 | De Riddler |
| 2006/0155340 A1 | 7/2006 | Schuler et al. |
| 2006/0206169 A1 | 9/2006 | Schuler |
| 2006/0218007 A1 | 9/2006 | Bjorner et al. |
| 2006/0224189 A1 | 10/2006 | Schuler et al. |
| 2006/0235472 A1 | 10/2006 | Goetz et al. |
| 2006/0259079 A1 | 11/2006 | King |
| 2006/0259099 A1 | 11/2006 | Goetz et al. |
| 2007/0000372 A1 | 1/2007 | Rezai et al. |
| 2007/0017749 A1 | 1/2007 | Dold et al. |
| 2007/0027514 A1 | 2/2007 | Gerber |
| 2007/0043268 A1 | 2/2007 | Russell |
| 2007/0049817 A1 | 3/2007 | Preiss et al. |
| 2007/0067003 A1 | 3/2007 | Sanchez et al. |
| 2007/0078498 A1 | 4/2007 | Rezai et al. |
| 2007/0083104 A1 | 4/2007 | Butson et al. |
| 2007/0123953 A1 | 5/2007 | Lee et al. |
| 2007/0129769 A1 | 6/2007 | Bourget et al. |
| 2007/0135855 A1 | 6/2007 | Foshee et al. |
| 2007/0150036 A1 | 6/2007 | Anderson |
| 2007/0156186 A1 | 7/2007 | Lee et al. |
| 2007/0162086 A1 | 7/2007 | Dilorenzo |
| 2007/0162235 A1 | 7/2007 | Zhan et al. |
| 2007/0168004 A1 | 7/2007 | Walter |
| 2007/0168007 A1 | 7/2007 | Kuzma et al. |
| 2007/0185544 A1 | 8/2007 | Dawant et al. |
| 2007/0191887 A1 | 8/2007 | Schuler et al. |
| 2007/0191912 A1 | 8/2007 | Ficher et al. |
| 2007/0197891 A1 | 8/2007 | Shachar et al. |
| 2007/0203450 A1 | 8/2007 | Berry |
| 2007/0203532 A1 | 8/2007 | Tass et al. |
| 2007/0203538 A1 | 8/2007 | Stone et al. |
| 2007/0203539 A1 | 8/2007 | Stone et al. |
| 2007/0203540 A1 | 8/2007 | Goetz et al. |
| 2007/0203541 A1 | 8/2007 | Goetz et al. |
| 2007/0203543 A1 | 8/2007 | Stone et al. |
| 2007/0203544 A1 | 8/2007 | Goetz et al. |
| 2007/0203545 A1 | 8/2007 | Stone et al. |
| 2007/0203546 A1 | 8/2007 | Stone et al. |
| 2007/0213789 A1 | 9/2007 | Nolan et al. |
| 2007/0213790 A1 | 9/2007 | Nolan et al. |
| 2007/0244519 A1 | 10/2007 | Keacher et al. |
| 2007/0245318 A1 | 10/2007 | Goetz et al. |
| 2007/0255321 A1 | 11/2007 | Gerber et al. |

(56) References Cited

U.S. PATENT DOCUMENTS

| | | |
|---|---|---|
| 2007/0255322 A1 | 11/2007 | Gerber et al. |
| 2007/0265664 A1 | 11/2007 | Gerber et al. |
| 2007/0276441 A1 | 11/2007 | Goetz |
| 2007/0282189 A1 | 12/2007 | Dan et al. |
| 2007/0288064 A1 | 12/2007 | Butson et al. |
| 2008/0027514 A1 | 1/2008 | DeMulling et al. |
| 2008/0039895 A1 | 2/2008 | Fowler et al. |
| 2008/0071150 A1 | 3/2008 | Miesel et al. |
| 2008/0081982 A1 | 4/2008 | Simon et al. |
| 2008/0086451 A1 | 4/2008 | Torres et al. |
| 2008/0103533 A1 | 5/2008 | Patel et al. |
| 2008/0123922 A1 | 5/2008 | Gielen et al. |
| 2008/0123923 A1 | 5/2008 | Gielen et al. |
| 2008/0133141 A1 | 6/2008 | Frost |
| 2008/0141217 A1 | 6/2008 | Goetz et al. |
| 2008/0154340 A1 | 6/2008 | Goetz et al. |
| 2008/0163097 A1 | 7/2008 | Goetz et al. |
| 2008/0183256 A1 | 7/2008 | Keacher |
| 2008/0188734 A1 | 8/2008 | Suryanarayanan et al. |
| 2008/0215118 A1 | 9/2008 | Goetz et al. |
| 2008/0227139 A1 | 9/2008 | Deisseroth et al. |
| 2008/0242950 A1 | 10/2008 | Jung et al. |
| 2008/0261165 A1 | 10/2008 | Steingart et al. |
| 2008/0269588 A1 | 10/2008 | Csavoy et al. |
| 2008/0300654 A1 | 12/2008 | Lambert et al. |
| 2009/0016491 A1 | 1/2009 | Li |
| 2009/0054950 A1 | 2/2009 | Stephens |
| 2009/0082640 A1 | 3/2009 | Kovach et al. |
| 2009/0082829 A1 | 3/2009 | Panken et al. |
| 2009/0112289 A1 | 4/2009 | Lee et al. |
| 2009/0118635 A1 | 5/2009 | Lujan et al. |
| 2009/0118786 A1 | 5/2009 | Meadows et al. |
| 2009/0149917 A1 | 6/2009 | Whitehurst et al. |
| 2009/0196471 A1 | 6/2009 | Goetz et al. |
| 2009/0196472 A1 | 8/2009 | Goetz et al. |
| 2009/0198306 A1 | 8/2009 | Goet et al. |
| 2009/0198354 A1 | 8/2009 | Wilson |
| 2009/0204192 A1 | 8/2009 | Carlton et al. |
| 2009/0210208 A1 | 8/2009 | McIntyre et al. |
| 2009/0242399 A1 | 10/2009 | Kamath et al. |
| 2009/0276008 A1 | 11/2009 | Lee et al. |
| 2009/0281595 A1 | 11/2009 | King et al. |
| 2009/0281596 A1 | 11/2009 | King et al. |
| 2009/0287271 A1 | 11/2009 | Blum et al. |
| 2009/0287272 A1 | 11/2009 | Kokones et al. |
| 2009/0287273 A1 | 11/2009 | Carlton et al. |
| 2009/0287467 A1 | 11/2009 | Sparks et al. |
| 2009/0299164 A1 | 12/2009 | Singhal et al. |
| 2009/0299165 A1 | 12/2009 | Sinhal et al. |
| 2009/0299380 A1 | 12/2009 | Singhal et al. |
| 2010/0010566 A1 | 1/2010 | Thacker et al. |
| 2010/0010646 A1 | 1/2010 | Drew et al. |
| 2010/0023103 A1 | 1/2010 | Elborno |
| 2010/0023130 A1 | 1/2010 | Henry et al. |
| 2010/0030312 A1 | 2/2010 | Shen |
| 2010/0049260 A1 | 2/2010 | Goetz |
| 2010/0049276 A1 | 2/2010 | Blum et al. |
| 2010/0064249 A1 | 3/2010 | Groetken |
| 2010/0113959 A1 | 5/2010 | Pascual-Leon et al. |
| 2010/0121409 A1 | 5/2010 | Kothandaraman et al. |
| 2010/0135553 A1 | 6/2010 | Joglekar |
| 2010/0137944 A1 | 6/2010 | Zhu |
| 2010/0152604 A1 | 6/2010 | Kuala et al. |
| 2010/0179562 A1 | 7/2010 | Linker et al. |
| 2010/0198315 A1 | 8/2010 | Martens et al. |
| 2010/0280579 A1 | 11/2010 | Denison et al. |
| 2010/0312303 A1 | 12/2010 | York et al. |
| 2010/0324410 A1 | 12/2010 | Paek et al. |
| 2010/0331883 A1 | 12/2010 | Schmitz et al. |
| 2011/0066407 A1 | 3/2011 | Butson et al. |
| 2011/0172737 A1 | 7/2011 | Davis et al. |
| 2011/0184487 A1 | 7/2011 | Alberts et al. |
| 2011/0191275 A1 | 8/2011 | Lujan et al. |
| 2011/0196253 A1 | 8/2011 | McIntyre et al. |
| 2011/0213440 A1 | 9/2011 | Fowler et al. |
| 2011/0306845 A1 | 12/2011 | Osorio |
| 2011/0306846 A1 | 12/2011 | Osorio |
| 2011/0307032 A1 | 12/2011 | Goetz et al. |
| 2012/0027272 A1 | 2/2012 | Akinyemi et al. |
| 2012/0046715 A1 | 2/2012 | Moffitt et al. |
| 2012/0078106 A1 | 3/2012 | Dentinger et al. |
| 2012/0089205 A1 | 4/2012 | Boyden et al. |
| 2012/0116476 A1 | 5/2012 | Kothandaraman |
| 2012/0165898 A1 | 6/2012 | Moffitt |
| 2012/0165901 A1 | 6/2012 | Zhu et al. |
| 2012/0172743 A1 | 7/2012 | Aguilar et al. |
| 2012/0207378 A1 | 8/2012 | Gupta et al. |
| 2012/0226138 A1 | 9/2012 | DeSalles et al. |
| 2012/0229468 A1 | 9/2012 | Lee et al. |
| 2012/0265262 A1 | 10/2012 | Osorio |
| 2012/0265268 A1 | 10/2012 | Blum et al. |
| 2012/0302912 A1 | 11/2012 | Moffitt et al. |
| 2012/0303087 A1 | 11/2012 | Moffitt et al. |
| 2012/0314924 A1 | 12/2012 | Carlton et al. |
| 2012/0316619 A1 | 12/2012 | Goetz et al. |
| 2013/0039550 A1 | 2/2013 | Blum et al. |
| 2013/0053722 A1 | 2/2013 | Carlson et al. |
| 2013/0060305 A1 | 3/2013 | Bokil |
| 2013/0116748 A1 | 5/2013 | Bokil et al. |
| 2013/0116749 A1 | 5/2013 | Carlton et al. |
| 2013/0116929 A1 | 5/2013 | Carlton et al. |
| 2014/0067018 A1 | 3/2014 | Carcieri et al. |
| 2014/0277284 A1 | 9/2014 | Chen et al. |
| 2015/0134031 A1 | 5/2015 | Moffitt et al. |

FOREIGN PATENT DOCUMENTS

| | | |
|---|---|---|
| EP | 1372780 | 1/2004 |
| EP | 1559369 | 8/2005 |
| WO | 97/39797 | 10/1997 |
| WO | 98/48880 | 11/1998 |
| WO | 01/90876 | 11/2001 |
| WO | 2001/90876 A1 | 11/2001 |
| WO | 02/26314 | 4/2002 |
| WO | 02/28473 | 4/2002 |
| WO | 02/065896 | 8/2002 |
| WO | 02/072192 | 9/2002 |
| WO | 03/086185 | 10/2003 |
| WO | 2004/019799 A2 | 3/2004 |
| WO | 2004041080 | 5/2005 |
| WO | 2006017053 | 2/2006 |
| WO | 2006113305 | 10/2006 |
| WO | 2007/097859 A1 | 6/2007 |
| WO | 2007/097861 A1 | 8/2007 |
| WO | 20071097859 | 8/2007 |
| WO | 20071097861 A1 | 8/2007 |
| WO | 2007/100427 | 9/2007 |
| WO | 2007/100427 A1 | 9/2007 |
| WO | 2007/100428 | 9/2007 |
| WO | 2007/100428 A1 | 9/2007 |
| WO | 2007/112061 | 10/2007 |
| WO | 2007/112061 A2 | 10/2007 |
| WO | 2009097224 | 8/2009 |
| WO | 2010/120823 A2 | 10/2010 |
| WO | 2011/139779 A1 | 11/2011 |
| WO | 2011/159688 A2 | 12/2011 |

OTHER PUBLICATIONS

McNaughtan et al., "Electrochemical Issues in Impedance Tomography", 1st World Congress on Industrial Process Tomography, Buxton, Greater Manchester, Apr. 14-17, 1999.

D'Haese et al., "Computer-Aided Placement of Deep Brain Stimulators: From Planning to Intraoperative Guidance", IEEE Transaction on Medical Imaging, 24:1469-1478, Nov. 2005.

Gross et al., "Electrophysiological Mapping for the Implantation of Deep Brain Stimulators for Parkinson's Disease and Tremor", Movement Disorders, 21 :S259-S283, Jun. 2006.

Halpern et al., "Brain Shift During Deep Brain Stimulation Surgery for Parkinson's Disease", Stereotact Funct. Neurosurg., 86:37-43, published online Sep. 2007.

(56) References Cited

OTHER PUBLICATIONS

Jeon et al., A Feasibility Study of Optical Coherence Tomography for Guiding Deep Brain Probes, Journal of Neuroscience Methods, 154:96-101, Jun. 2006.
Ericsson, A. et al., "Construction of a patient-specific atlas of the brain: Application to normal aging," Biomedical Imaging: From Nano to Macro, ISBI 2008, 5th IEEE International Symposium, May 14, 2008, pp. 480-483.
Kaikai Shen et al., "Atlas selection strategy using least angle regression in multi-atlas segmentation propagation," Biomedical Imaging: From Nano Macro, 2011, 8th IEEE International Symposium, ISBI 2011, Mar. 30, 2011, pp. 1746-1749.
Liliane Ramus et al., "Assessing selection methods in the cotnext of multi-atlas based segmentation," Biomedical Imaging: From Nano to Macro, 2010, IEEE International Symposium, Apr. 14, 2010, pp. 1321-1324.
Olivier Commowick et al., :"Using Frankenstein's Creature Paradigm to Build a Patient Specific Atlas," Sep. 20, 2009, Medical Image Computing and Computer-Assisted Intervention, pp. 993-1000.
Loijonen J.M.P . et al., "Fast and robust multi-atlas segmentation of brain magnetic resonance images," NeuroImage, Academic Press. vol. 49, No. 3, Feb. 1, 2010, pp. 2352-2365.
Khan et al., "Assessment of Brain Shift Related to Deep Brain Stimulation Surgery", Sterreotact Funct. Neurosurg., 86:44-53, published online Sep. 2007.
Sanchez Castro et al., "A cross validation study of deep brain stimulation targeting: From experts to Atlas-Based Segmentation-Based and Automatic Registration Algorithms," IEEE Transactions on Medical Imaging, vol. 25, No. 11, Nov. 1, 2006, pp. 1440-1450.
Koop et al., "Improvement in a Quantitative Measure of Bradykinesia After Microelectrode Recording in Patients with Parkinson's Disease During Deep Brain Stimulation Surgery", Movement Disorders, 21 :673-678, published on line Jan. 2006.
Lemaire et al., "Brain Mapping in Stereotactic Surgery: A Brief Overview from the Probabilistic Targeting to the Patient-Based Anatomic Mapping", NeuroImage, 37:S109-3115, available online Jun. 2007.
Machado et al., "Deep Brain Stimulation for Parkinson's Disease: Surgical Technique and Perioperative Management", Movement Disorders, 21 :S247-S258, Jun. 2006.
Maks et al., "Deep Brain Stimulation Activation Volumes and Their Association with Neurophysiological Mapping and Therapeutic Outcomes", Downloaded from jnnp.bmj.com, pp. 1-21, published online Apr. 2008.
Moran et al., "Real-Time Refinment of Subthalamic Nucleous Targeting Using Bayesian Decision-Making on the Root Mean Square Measure", Movement Disorders, 21: 1425-1431, published online Jun. 2006.
Sakamoto et al., "Homogeneous Fluorescence Assays for RNA Diagnosis by Pyrene-Conjugated 2'-0-Methyloligoribonucleotides", Nucleosides, Nucleotides, and Nucleric Acids, 26:1659-1664, on line publication Oct. 2007.
Winkler et al., The First Evaluation of Brain Shift During Functional Neurosurgery by Deformation Field Analysis, J. Neural. Neurosurg. Psychiatry, 76:1161-1163, Aug. 2005.
Siegel, Ralph M. et al., "Spatiotemporal dynamics of the functional architecture for gain fields in inferior parietal lobule of behaving monkey," Cerebral Cortex, New York, NY, vol. 17, No. 2, Feb. 2007, pp. 378-390.
Klein, A. et al., "Evaluation of 14 nonlinear deformation algorithms applied to human brain MRI registration." NeuroImage, Academic Press, Orlando, FL, vol. 46, No. 3, Jul. 2009, pp. 786-802.
Yelnik et al., "A Three-Dimensional, Histological and Deformable Atlas of the Human Basal J Ganglia, I. Atlas Construction Based on Immunohistochemical and MRI Data", NeuroImage, 34:618-638,Jan. 2007.
Ward, H. E. et al., "Update on deep brain stimulation for neuropsychiatric disorders." Neurobiol Dis 38 (3) (2010), pp. 346-353.

Alberts et al. "Bilateral subthalamic stimulation impairs cognitive-motor performance in Parkinson's disease patients." Brain (2005), 131, 3348-3360, Abstract.
Izad, Oliver. "Computationally Efficient Method in Predicating Axonal Excitation," Dissertation for Master Degree, Department of Biomedical Engineering, Case Western Reserve University, May 2009.
Jaccard, Paul, "Elude comparative de la distribution florale dans une portion odes Aples et des Jura," Bulletin de la Societe Vaudoise des Sciences Naturelles (1901), 37:547-579.
Dice, Lee R., "Measures of the Amount of Ecologic Association Between Species," Ecology 26(3) (1945): 297-302. doi:10.2307/1932409, http://jstor.org/stable/1932409.
Rand, WM., "Objective criteria for the evaluation of clustering methods," Journal of the American Statistical Association (American Statistical Association) 66 (336) (1971 ): 846-850, doi:10.2307/2284239, http://jstor.org/stable/2284239.
Hubert, Lawrence et al., "Comparing partitions," Journal of Classification 2(1) (1985): 193-218, doi:10.1007/BF01908075.
An, et al., "Prefronlal cortical projections to longitudinal columns in the midbrain periaqueductal gray in macaque monkeys," J Comp Neural 401 (4) (1998), pp. 455-479.
Melia, Marina, "Comparing Clusterings by the Variation of Information," Learning Theory and Kernel Machines (2003): 173-187.
Carmichael, S. T., et al., "Connectional networks within the orbital and medial prefronlal cortex of macaque monkeys," J Comp Neural 371 (2) (1996), pp. 179-207.
Croxson, et al., "Quantitative investigation of connections of the prefronlal cortex in the human and macaque using probabilistic diffusion tractography," J Neurosci 25 (39) (2005), pp. 8854-8866.
Frankemolle, et al., "Reversing cognitive-motor impairments in Parkinson's disease patients using a computational modelling approach to deep brain stimulation programming," Brain 133 (2010), pp. 746-761.
Freedman, et al., "Subcortical projections of area 25 (subgenual cortex) of the macaque monkey," J Comp Neurol 421 (2) (2000), pp. 172-188.
Giacobbe, et al., "Treatment resistant depression as a failure of brain homeostatic mechanisms: implications for deep brain stimulation," Exp Neural 219 (1) (2009), pp. 44-52.
Schmidt et al. "Sketching and Composing Widgets for 3D Manipulation," Eurographics, Apr. 2008, vol. 27, No. 2, pp. 301-310.
Goodman, et al., "Deep brain stimulation for intractable obsessive compulsive disorder: pilot study using a blinded, staggered-onset design," Biol Psychiatry 67 (6) (2010), pp. 535-542.
Greenberg, et al., "Deep brain stimulation of the ventral internal capsule/ventral striatum for obsessive-compulsive disorder: worldwide experience," Mol Psychiatry 15 (1) (2010), pp. 64-79.
Greenberg. et al., "Three-year outcomes in deep brain stimulation for highly resistant obsessive-compulsive disorder," Neuropsychopharmacology 31 (11) (2006), pp. 2384-2393.
Gutman, et al., "A tractography analysis of two deep brain stimulation white matter targets for depression," Biol Psychiatry 65 (4) (2009), pp. 276-282.
Haber, et al., "Reward-related cortical inputs define a large striatal region in primates that interface with associative cortical connections, providing a substrate for incentive-based learning," J Neurosci 26 (32) (2006), pp. 8368-8376.
Haber, et al., "Cognitive and limbic circuits that are affected by deep brain stimulation," Front Biosci 14 (2009), pp. 1823-1834.
Hua, et al., "Tract probability maps in stereotaxic spaces: analyses of white matter anatomy and tract-specific quantification," NeuroImage 39 (1) (2008), pp. 336-347.
Johansen-Berg, et al., "Anatomical connectivity of the subgenual cingulate region targeted with deep brain stimulation for treatment-resistant depression," Cereb Cortex 18 (6) (2008), pp. 1374-1383.
Kopell, et al., "Deep brain stimulation for psychiatric disorders," J Clin Neurophysiol 21 (1) (2004), pp. 51-67.
Lozano, et al., "Subcallosal cingulate gyrus deep brain stimulation for treatment-resistant depression," Biol Psychiatry 64 (6) (2008), pp. 461-467.

(56) References Cited

OTHER PUBLICATIONS

Lujan, et al., "Tracking the mechanisms of deep brain stimulation for neuropsychiatric disorders," Front Biosci 13 (2008), pp. 5892-5904.
Lujan, J.L. et al., "Automated 3-Dimensional Brain Atlas Fitting to Microelectrode Recordings from Deep Brain Stimulation Surgeries," Stereotact. Funel. Neurosurg. 87(2009), pp. 229-240.
Fisekovic et al., "New Controller for Functional Electrical Stimulation Systems", Med. Eng. Phys. 2001; 23:391-399.
Zhang, Y., et al., "Atlas-guided tract reconstruction for automated and comprehensive examination of the white matter anatomy," Neuroimage 52(4) (2010), pp. 1289-1301.
Machado, et al., "Functional topography of the ventral striatum and anterior limb of the internal capsule determined by electrical stimulation of awake patients," Clin Neurophysiol 120 (11) (2009), pp. 1941-1948.
Malone, et al., "Deep brain stimulation of the ventral capsule/ventral striatum for treatment-resistant depression," Biol Psychiatry 65 (4) (2009), pp. 267-275.
Carnevale, N.T. et al., "The Neuron Book," Cambridge, UK: Cambridge University Press (2006), 480 pages.
Mouine et al. "Multi-Strategy and Multi-Algorithm Cochlear Prostheses", Biomed. Sci. Instrument, 2000; 36:233-238.
Jones et al., "An Advanced Demultiplexing System for Physiological Stimulation", IEEE Transactions on Biomedical Engineering, vol. 44 No. 12 Dec. 1997. pp. 1210-1220.
Frankemolle, et al., "Reversing cognitive-motor impairments in Parkinson's disease patients using a computational modeling approach to deep brain stimulation programming," Brian 133 (2010), pp. 746-761.
McIntyre, C.C., et al., "Modeling the excitablitity of mammalian nerve fibers: influence of afterpotentials on the recovery cycle," J Neurophysiol, 87(2) (Feb. 2002), pp. 995-1006.
Peterson, et al., "Predicting myelinated axon activation using spatial characteristics of the extracellular field," Journal of Neural Engineering, 8 (2011), 12 pages.
Mayberg, H. S., et el., "Limbic-cortical dysregulation: a proposed model of depression," J Neuropsychiatry Clin Neurosci. 9 (3) (1997), pp. 471-481.
Wesselink, et al., "Analysis of Current Density and Related Parameters in Spinal Cord Stimulation," IEEE Transactions on Rehabilitation Engineering, vol. 6, No. 2 Jun. 1998, pp. 200-207.
McIntyre,C. C., et al., "Network perspectives on the mechanisms of deep brain stimulation," Neurobiol Dis 38 (3) (2010), pp. 329-337.
Miocinovic, S., et al., "Experimental and theoretical characterization of the voltage distribution generated by deep brain stimulation," Exp Neurol 216(I) (2009), pp. 166-176.
Bazin et al., "Free Software Tools for Atlas-based Volumetric Neuroimage Analysis", Proc. SPIE 5747, Medical Imaging 2005: Image Processing, 1824 May 5, 2005.
Nuttin, et al., "Electrical stimulation in anterior limbs of internal capsules in patients with obsessive-compulsive disorder," Lancet 354 (9189) (1999), p. 1526.
Saxena, et al., "Cerebral glucose metabolism in obsessive-compulsive hoarding," Am J Psychiatry. 161 (6) (2004), pp. 1038-1048.
Brown, J. "Motor Cortex Stimulation," Neurosurgical Focus ( Sep. 15, 2001) 11(3):E5.
Budai et al., "Endogenous Opioid Peptides Acting at m-Opioid Receptors in the Dorsal Horn Contribute to Midbrain Modulation of Spinal Nociceptive Neurons," Journal of Neurophysiology (1998) 79(2): 677-687.
Cesselin, F. "Opioid and ant-opioid peptides," Fundamental and Clinical Pharmacology (1995) 9(5): 409-33 (Abstract only).
Rezai et al., "Deep Brain Stimulation for Chronic Pain" Surgical Management of Pain, Chapter 44 pp. 565-576.
Xu, MD., Shi-Ang, article entitled "Comparison of Half-Band and Full-Band Electrodes for Intracochlear Electrical Stimulation", Annals of Otology, Rhinology & Laryngology (Annals of Head & Neck Medicine & Surgery), vol. 102 (5) pp. 363-367 May 1993.
Viola, et al., "Importance-driven focus of attention," IEEE Trans Vis Comput Graph 12 (5) (2006), pp. 933-940.
Mayr et al., "Basic Design and Construction of the Vienna FES Implants: Existing Solutions and Prospects for New Generations of Implants", Medical Engineering & Physics, 2001; 23:53-60.
Dawant, B. M., et al., "Computerized atlas-guided positioning of deep brain stimulators: a feasibility study," Biomedical Image registration, Second International Workshop, WBIR 2003, Revised Papers (Lecture notes in Comput. Sci. vol. (2717), Springer-Verlag Berlin, Germany (2003), pp. 142-150.
Gross, R.E., et al., "Advances in neurostimulation for movement disorders," Neurol Res., 22(3) (Apr. 2000), pp. 247-258.
D'Haese et al. Medical Image Computing and Computer-Assisted Intervention—MICCAI 2005 Lecture Notes in Computer Science, 2005, vol. 3750, 2005, 427-434.
Rohde et al. IEEE Transactions on Medical Imaging, vol. 22 No. 11, 2003 p. 1470-1479.
Miocinovic et al., "Stereotactive Neurosurgical Planning, Recording, and Visualization for Deep Brain Stimulation in Non-Human Primates", Journal of Neuroscience Methods, 162:32-41, Apr. 5, 2007, XP022021469.
Gemmar et al., "Advances Methods for Target Navigation Using Microelectrode Recordings in Stereotactic Neurosurgery for Deep Brain Stimulation", 21st IEEE International Symopsium on Computer-Based Medical Systems, Jun. 17, 2008, pp. 99-104, XP031284774.
Acar et al., "Safety Anterior Commissure-Posterior Commissure-Based Target Calculation of the Subthalamic Nucleus in Functional Stereotactic Procedures", Stereotactic Funct. Neurosura., 85:287-291, Aug. 2007.
Andrade-Souza, "Comparison of Three Methods of Targeting the Subthalamic Nucleus for Chronic Stimulation in Parkinson's Disease", Neurosurgery, 56:360-368, Apr. 2005.
Anheim et al., "Improvement in Parkinson Disease by Subthalamic Nucleus Stimulation Based on Electrode Placement", Arch Neural, 65:612-616, May 2008.
Nowak, LG., et al., "Axons, but not cell bodies, are activated by electrical stimulation in cortical gray matter. I. Evidence from chronaxie measurements," Exp. Brain Res., 118(4) (Feb. 1998), pp. 477-486.
Wakana, S., et al., "Fiber tract-based atlas of human white matter anatomy," Radiology, 230(1) (Jan. 2004), pp. 77-87.
Voghell et al., "Programmable Current Source Dedicated to Implantable Microstimulators" ICM '98 Proceedings of the Tenth International Conference, pp. 67-70.
Butson et al., "Current Steering to Control the Volume of Tissue Activated During Deep Brain Stimulation," Brain Stimulation 1, 2008, pp. 7-15.
Butson et al., "Patient Specific Analysis of the volume of tissue activated during deep brain stimulation," NeuroImage, Academic Press, vol. 34, No. 2, Dec. 2. 2006, pp. 661-670.
Butson et al., "Role of Electrode Design on the Volume of Tissue Activated During Deep Brain Stimulation," Journal of Neural Engineering, Mar. 1, 2006, vol. 3, No. 1, pp. 1-8.
Butson et al., "StimExplorer: Deep Brain Stimulation Parameter Selection Software System," Acta Neurochirugica, Jan. 1, 2007, vol. 97, No. 2, pp. 569-574.
Cover, T.M. et al., "Elements of information theory," (1991) John Wiley & Sons, New York, NY, pp. 1-542.
Dice, LeeR., "Measures of the Amount of Ecologic Association Between Species," Ecology 26(3) (1945), pp. 297-302, doi:1 0.2307/1932409, http:l/jstor.org/stable/1932409.
European Patent Office, International Search Report in International Application No. PCT/US2012/053344, dated Nov. 26, 2012. 8 pages.
European Patent Office. International Search Report in International Application No. PCT/US2012/050181, dated Jan. 3, 2013, 7 pages.
European Patent Office, International Search Report and the Written Opinion in International Application No. PCT/US2012/050170, dated Oct. 5, 2012, 15 pages.
European Patent Office, International Search Report in International Application No. PCT/US09/03017, dated Aug. 3, 2009, 7 pages.

(56) References Cited

OTHER PUBLICATIONS

European Patent Office, International Search Report in International Application No. PCT/US09/03038, dated Oct. 8, 2009, 9 pages.
European Patent Office, International Search Report in International Application No. PCT/US09/03040, dated Aug. 13, 2009, 7 pages.
European Patent Office, International Search Report in International Application No. PCT/US09/03049, dated Jan. 26, 2010, 8 pages.
European Patent Office, partial International Search Report in International Application No. PCT/US2012/030701, dated Feb. 15, 2013, 7 pages.
European Patent Office, partial International Search Report in International Application No. PCT/US2012/030705, dated Mar. 6, 2013, 7 pages.
European Patent Office, International Search report and Written Opinion in PCT application No. PCT/US12/050174, dated Mar. 6, 2013, 20 pages.
European Patent Office, International Search Report and Written Opinion in International Application No. PCT/US2012/050187, dated Feb. 27, 2013, 9 pages.
European Patent Office. International Search Report and Written Opinion in International Application No. PCT/US2012/030700, dated Feb. 27, 2013, 9 pages.
European Patent Office, International Search Report in International Application No. PCT/US09/03041, dated Aug. 20, 2009, 7 pages.
European Patent Office, International Search Report and Written Opinion of the International Searching Authority in International Application No. PCT/US2012/050175, dated Oct. 26, 2012, 15 pages.
Hubert, Lawrence et al., "Comparing partitions," Journal of Classification 2(1) (1985), pp. 193-218, doi:10.1 007/BF01908075.
Izad, Olivier, "Computationally Efficient Method in Predicating Axonal Excitation," Dissertation for Masters Degree, Department of Biomedical Engineering, Case Western Reserve University, May 2009, 144 pages.
Jaccard, Paul, "Etude comparative de la distribution ftorale dans une portion odes Aples el des Jura," Bulletin de la Societe Vaudoise des Sciences Naturelles (1901), vol. 37, pp. 547-579.
Kaikai Shen et al., "Atlas selection strategy using least angle regression in multi-atlas segmentation propagation," 26 Biomedical Imaging: From Nano to Macro, 2011, 8th IEEE International Symposium, ISBI 2011, Mar. 30, 2011, pp. 1746-1749.
Klein, A. et al., "Evaluation of 14 nonlinear deformation algorithms applied to human brain MRI registration," NeuroImage, Academic Press, Orlando, FL, vol. 46, No. 3, Jul. 2009, pp. 786-803.
Liliane Ramus et al, "Assessing selection methods in the context of multi-atlas based segmentation," Biomedical Imaging: From Nano to Macro, 2010 IEEE International Symposium, Apr. 14, 2010, pp. 1321-1324.
Lotjonen J.M.P. et al, "Fast and robust multi-atlas segmentation of brain magnetic resonance images," NeuroImage, Academic Press, vol. 49, No. 3, Feb. 1, 2010. pp. 2352-2365.
Mcintyre. C. C., et al., "Modeling the excitability of mammalian nerve fibers: influence of afterpotentials on the recovery cycle," J Neurophysiol, 87(2) (Feb. 2002), pp. 995-1006.
Meila, Marina, "Comparing Clusterings by the Variation of Information," Learning Theory and Kernel Machines (2003), pp. 173-187.
Miocinovic et al., "Cicerone: Stereotactic Neurophysiological Recording and Deep Brain Stimulation Electrode Placement Software System," Acta Neurochirurgica Suppl., Jan. 1, 2007, vol. 97, No. 2, pp. 561-567.
Olivier Commowick et al., "Using Frankenstein's Creature Paradigm to Build a Patient Specific Atlas," Sep. 20, 2009, Medical Image Computing and Computer-Assisted Intervention, pp. 993-1000.
Rand, W.M., "Objective criteria for the evaluation of clustering methods," Journal of the American Statistical 34 Association (American Statistical Association) 66 (336) (1971 ), pp. 846-850, doi:10.2307/2284239, http://jstor.org/stable/2284239.
Sanchez Castro et al., "A cross validation study of deep brain stimulation targeting: From experts to Atlas-Based, 35 Segmentation-Based and Automatic Registration Algorithms," IEEE Transactions on Medical Imaging, vol. 25, No. 11, Nov. 1, 2006, pp. 1440-1450.
Schmidt et al., "Sketching and Composing Widgets for 3D Manipulation," Eurographics, Apr. 2008, vol. 27, No. 2, pp. 301-310.
Warman, et al., "Modeling the Effects of Electric Fields on nerve Fibers: Determination of Excitation Thresholds," IEEE Transactions on Biomedical Engineering, vol. 39, No. 12 (Dec. 1992), pp. 1244-1254.
Peterson et al., "Predicting myelinated axon activation using spatial characteristics of the extracellular field," Journal of Neural Engineering, 8 (2011), 12 pages.
U.S. Appl. No. 12/029,141, filed Feb. 11, 2008.
Volkmann et al., Introduction to the Programming of Deep Brain Stimulators, Movement Disorders, vol. 17, Suppl. 3, pp. S181-S187 (2002).
Official Communication, U.S. Appl. No. 13/973,113, dated Feb. 5, 2016, 20 pages.
Official Communication, U.S. Appl. No. 13/973,113, dated Aug. 12, 2016, 16 pages.

* cited by examiner

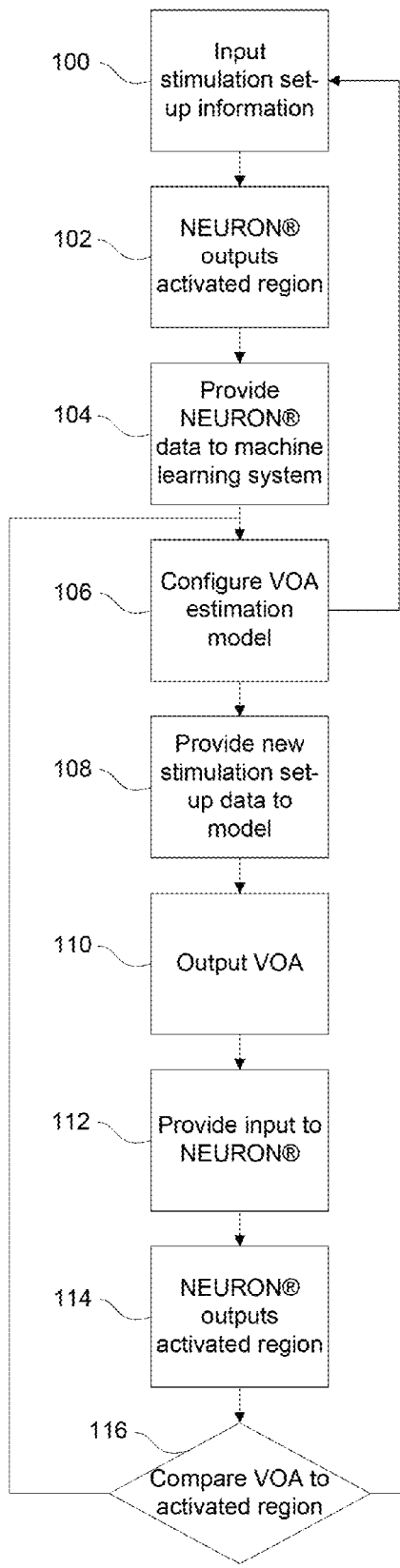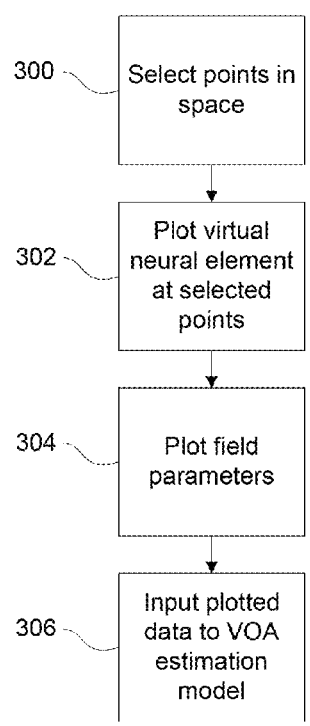
Fig. 1
Fig. 3

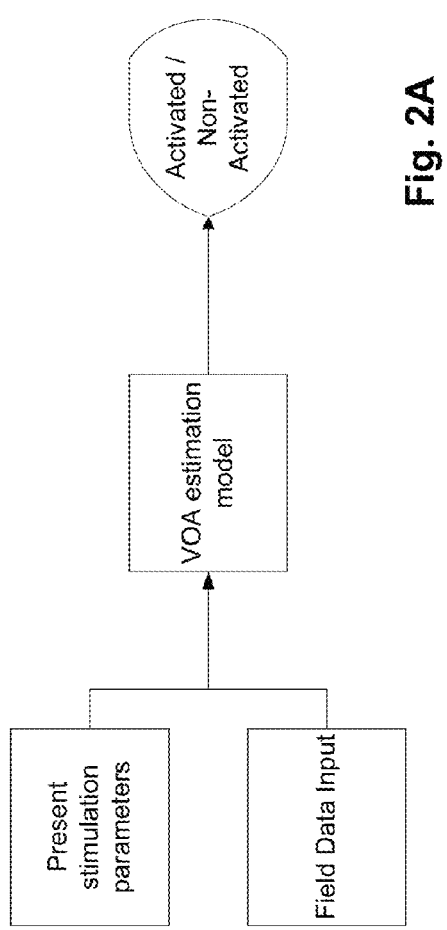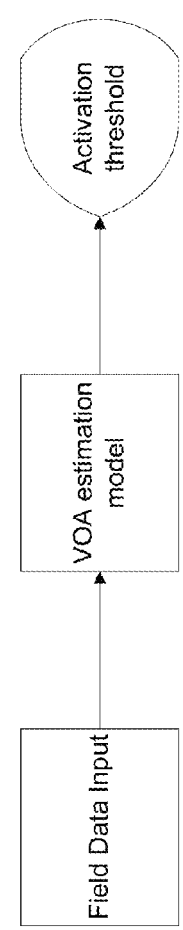

SYSTEMS AND METHODS FOR VOA MODEL GENERATION AND USE

CROSS-REFERENCE TO RELATED APPLICATIONS

The present application is a continuation of U.S. patent application Ser. No. 13/973,113 filed Aug. 22, 2013 which claims priority to U.S. Provisional Patent Application Ser. No. 61/721,112 filed on Nov. 1, 2012, the contents of all of which are hereby incorporated by reference herein in their entirety.

FIELD OF THE INVENTION

Aspects of the present invention pertain to generation of a model that outputs a representation of an estimated volume of tissue activated (VOA) or its isosurface in response to input parameters that are representative of a stimulation applied by an implanted leadwire. Aspects of the present invention also separately and/or additionally pertain to use of one or more types of data representative of values at a plurality of locations along each of a plurality of anatomical elements, e.g., neural elements, as input to a model that accordingly outputs a VOA covering those of the elements estimated to be activated with an applied stimulation to which the data corresponds.

BACKGROUND INFORMATION

Stimulation of anatomical regions of a patient is a clinical technique for the treatment of disorders. Such stimulation can include deep brain stimulation (DBS), spinal cord stimulation (SCS), Occipital NS therapy, Trigemenal NS therapy, peripheral field stimulation therapy, sacral root stimulation therapy, or other such therapies. For example, DBS may include electrical stimulation of the thalamus or basal ganglia and may be used to treat disorders such as movement disorders such as essential tremor, Parkinson's disease (PD), and dystonia, and other physiological disorders. DBS may also be useful for traumatic brain injury and stroke. Pilot studies have also begun to examine the utility of DBS for treating depression, obesity, epilepsy, and obsessive-compulsive disorder, Tourette's Syndrome, schizophrenia, and other indications.

A stimulation procedure, such as DBS, typically involves first obtaining preoperative images, e.g., of the patient's brain, such as by using a computed tomography (CT) scanner device, a magnetic resonance imaging (MRI) device, or any other imaging modality. This sometimes involves first affixing to the patient's skull spherical or other fiducial markers that are visible on the images produced by the imaging modality. The fiducial markers help register the preoperative images to the actual physical position of the patient in the operating room during the later surgical procedure.

After the preoperative images are acquired by the imaging modality, they are then loaded onto an image-guided surgical (IGS) workstation, and, using the preoperative images displayed on the IGS workstation, a neurosurgeon can select a target region within the patient anatomy, e.g., within the brain, an entry point, e.g., on the patient's skull, and a desired trajectory between the entry point and the target region. The entry point and trajectory are typically carefully selected to avoid intersecting or otherwise damaging certain nearby critical structures or vasculature.

In the operating room, the physician marks the entry point on the patient's skull, drills a burr hole at that location, and affixes a trajectory guide device about the burr hole. The trajectory guide device includes a bore that can be aimed to obtain the desired trajectory to the target region. After aiming, the trajectory guide is locked to preserve the aimed trajectory toward the target region. After the aimed trajectory has been locked in using the trajectory guide, a microdrive introducer is used to insert the surgical instrument along the trajectory toward the target region, e.g., of the brain. The surgical instrument may include, among other things, a recording electrode leadwire, for recording intrinsic electrical signals, e.g., of the brain; a stimulation electrode leadwire, for providing electrical energy to the target region, e.g., of the brain; or associated auxiliary guidewires or guide catheters for steering a primary instrument toward the target region, e.g., of the brain.

The stimulation electrode leadwire, which typically includes multiple closely-spaced electrically independent stimulation electrode contacts, is then introduced and positioned in close proximity to the tissue targeted for sitmulation, to deliver the therapeutic stimulation to the target region, e.g., of the brain. An implanted pulse generator (IPG) generates electric pulses to transmit signals via the leadwire. The leadwire can include cylindrically symmetrical electrodes, which, when operational, produce approximately the same electric values in all positions at a same distance from the electrode in any plain that cuts through the electrode perpendicular to the central longitudinal axis of the leadwire. Alternatively, the leadwire can include directional electrodes that produce different electrical values depending on the direction from the electrode. The stimulation electrode leadwire is then immobilized, such as by using an instrument immobilization device located at the burr hole entry, e.g., in the patient's skull, in order for the DBS therapy to be subsequently performed.

The target anatomical region can include tissue that exhibit high electrical conductivity. For a given stimulation parameter setting, a respective subset of the neural elements are responsively activated. A stimulation parameter can include, for example, a current amplitude or voltage amplitude, which may be the same for all of the electrodes of the leadwire, or which may vary between different electrodes of the leadwire. The applied amplitude setting results in a corresponding current in the surrounding neural elements, and therefore a corresponding voltage distribution in the surrounding tissue.

After the immobilization of the stimulation electrode leadwire, the actual stimulation therapy is often not initiated until after a time period of about two-weeks to one month has elapsed. This is due primarily to the acute reaction of the brain tissue to the introduced electrode leadwire (e.g., the formation of adjacent scar tissue), and stabilization of the patient's disease symptoms. At that time, a particular one or more of the stimulation electrode contacts is selected for delivering the therapeutic stimulation, and other stimulation parameters are adjusted to achieve an acceptable level of therapeutic benefit. The IPGs offer a wide range of stimulation settings which can be independently or concurrently varied in order to correspondingly alter the size, shape, and location of the volume of tissue being therapeutically affected by the stimulation.

Systems and methods are provided that facilitate exploration of target regions of stimulation and stimulation therapies to determine which therapy regimen is best suited for a particular patient or group of patients.

A treating physician typically would like to tailor the stimulation parameters (such as which one or more of the stimulating electrode contacts to use, the stimulation pulse amplitude, e.g., current or voltage depending on the stimulator being used, the stimulation pulse width, and/or the stimulation frequency) for a particular patient to improve the effectiveness of the therapy. Parameter selections for the stimulation can be achieved, for example, via trial-and-error. However, the use of guiding visualization software provides for efficient stimulation parameter selection. See Frankemolle, A. et al., "Reversing cognitive-motor impairments in Parkinson's disease patients using a computational modelling approach to deep brain stimulation programming," Brain 133 (3): 746-761 (2010). Indeed, systems and methods are provided that provide visual aids of the electrode location in the tissue medium along with computational models of the volume of tissue influenced by the stimulation, thereby facilitating parameter selection. See, for example, U.S. patent application Ser. No. 12/454,330, filed May 15, 2009 ("the '330 application"), U.S. patent application Ser. No. 12/454,312, filed May 15, 2009 ("the '312 application"), U.S. patent application Ser. No. 12/454,340, filed May 15, 2009 ("the '340 application"), U.S. patent application Ser. No. 12/454,343, filed May 15, 2009 ("the '343 application"), and U.S. patent application Ser. No. 12/454,314, filed May 15, 2009 ("the '314 application"), the content of each of which is hereby incorporated herein by reference in its entirety. Those applications describe systems including equation-based models for generation of VOAs based on input of stimulation parameters. The described systems and methods provide for estimation of stimulation volumes and display models of a patient anatomy and/or a stimulation leadwire, via which to graphically identify the estimated stimulation volumes and how they interact with various regions of the patient anatomy. If a physician selects a putative therapeutic stimulation parameter combination, the software displays a representation of the volume of surrounding tissue which is estimated to be activated by the system. See also S. Miocinovic et al., "Cicerone: stereotactic neurophysiological recording and deep brain stimulation electrode placement software system," Acta Neurochir. Suppl. 97(2): 561-567 (2007).

U.S. Prov. Pat. App. Ser. Nos. 61/521,583 ("the '583 application"), filed Aug. 9, 2011 and 61/690,270 ("the '270 application"), filed Jun. 22, 2012, each of which is hereby incorporated by reference in its entirety, further describe generation of a VOA on a fiber specific basis.

SUMMARY

Embodiments of the present invention provide an improved estimation model for use to generate VOAs. Example embodiments provide a VOA generation model that accepts as input, values of a same parameter at multiple locations along a single neural element, e.g., a fiber, an axon, a neuron, etc., the input values corresponding to a particular set of stimulation settings, e.g., which of the electrodes are activated, their respective powers, pulse width, etc., and produces, based on such input, a VOA (or isosurface encompassing the VOA). The multiple input values may be of a same single data type. For example, they can all be voltage values at the different positions of the neural element, for example, of an electric field produced by the particular set of stimulation settings. Alternatively, they can all be, for example, activating function (AF) values, i.e., values of a second central difference of the voltage at the center of each node of Ranvier of each fiber. In an example embodiment, a test neural element is plotted (the term "plot," as used herein, refers to an internal association of data values with spatial coordinates, and need not include the output of a graphical representation of such an association) at each of a plurality of points about the leadwire and input into the estimation model for determination of whether the respective points are estimated to be activated at the given stimulation parameter settings. An example appropriate test neural element includes approximately 21 nodes. See "Modeling the Excitability of Mammalian Nerve Fibers: Influence of Afterpotentials on the Recovery Cycle," Cameron C. McIntyre et al., *J Neurophysiol.,* 87:995-1006 (2002). However, neural elements having fewer or a greater number of nodes can be used. Additionally, other data types can be used instead.

In this regard, previous generations of prediction algorithms have employed two or fewer scalar values of different type in order to classify a particular fiber as activated by the given stimulation settings. For example, the '583 and '270 applications refer to a model that accepts as input scalar values for two data types at a single respective position along a neural element. However, the inventors of the present application have discovered that an estimation model that accepts values of the same single type taken along two or more positions of a neural element provides a more accurate VOA. Specifically, such a model more accurately estimates whether the relevant neural element is activated than a model that accepts only one value for each of two different data types per relevant neural element. Moreover, the multiple values of the same data type at respective multiple locations of a considered neural element are indicative of the value gradations in space, allowing for an estimation even in the case of directional leadwires.

In an example embodiment, the model accepts values for each of more than one data type for each of the plurality of locations of the relevant neural element. For example, the model accepts, for each of the plurality of locations along the considered neural element, a voltage value and an AF value as suggested in the '583 and '270 applications for a single location of the neural element. In an example embodiment, based on the model determinations of activation for each of the considered neural elements, the system draws as the VOA a volume encompassing all of the neural elements the model has estimated to be activated.

VOA generation models have been previously suggested, for example, as taught in the '330, '312, '340, '343, and '314 applications. Often the generation of the models are such that different models must be generated for a specific stimulation leadwire type. For example, if a model is generated for a symmetrically cylindrical leadwire, a different model would have to be generated for a directional leadwire. This adds burden to the process of introducing new leadwires to the market and affects decisions on leadwire development. Moreover, while some of the previously generated models provide substantially accurate VOAs for parameters of cylindrically symmetrical leadwires, they are indeed not usable for directional leadwires. For example, the previously generated models rely on a set of assumptions which include the cylindrical symmetry of the leadwire and specifics of the geometry of the leadwire, and therefore new models are required.

Example embodiments of the present invention provide for a better model generation method, which produces a model that outputs VOAs for various types of leadwire designs, including both cylindrically symmetrical and directional type leadwires, and which requires less restrictive assumptions, for example, which do not require the assumption of symmetry of the values cylindrically about an electrode at a given outer radius. Such a model would be more general than current models and would support new symmetric, directional, and arbitrary leadwires. Specifically, example embodiments of the present invention provide for use of machine learning (ML) for automatic (or partially automatic) generation of an estimation model that outputs a VOA for a given input.

Accordingly, example embodiments of the present invention use machine learning techniques to generate a model that predicts the activation threshold and/or the activation classification (activated or not activated) by considering field data (scalar or vector) of electrical parameters (e.g., voltage, current, derivatives, densities) in a uni- or multi-dimensional space. The machine learning based estimation model can support a robust and changing portfolio of leadwires.

Example embodiments of the present invention provide for use of machine learning to generate a model that accepts as input for each of a plurality of neural elements, data of a single type for each of a plurality of locations of the respective neural element, estimates for each of the neural elements and based on such data whether the respective neural element is activated, and provides for a visual two- or three-dimensional representation of an area including those of the neural elements estimated to be activated and excluding those of the neural elements positioned, with respect to the leadwire, beyond the farthest of those of the neural elements estimated to be activated. The combination of the use of machine learning to generate the estimation model with the estimation model accepting as input data of a selected type at multiple locations of the considered neural element further provides for the resulting estimation model to be usable for estimating VOAs for parameter settings of different kinds of leadwires.

Alternative example embodiments of the present invention provide for determining activation thresholds at the plurality of locations, without performing the following step of determining whether the neural elements are activated. For example, in an example embodiment the model outputs a firing threshold(s) based on normalized input data. A different module can then be used based on the threshold(s) to determine which neural elements are estimated to fire based on currently set settings.

Alternative example embodiment of the present invention provide for use of machine learning to generate a model such as that described above, but that accepts as input for each of a plurality of neural elements, data of each of multiple types for each of the plurality of locations of the respective neural element.

The various methods described herein may be practiced, each alone, or in various combinations.

An example embodiment of the present invention is directed to a processor, which can be implemented using any conventional processing circuit and device or combination thereof, e.g., a Central Processing Unit (CPU) of a Personal Computer (PC) or other workstation processor, to execute code provided, e.g., on a hardware computer-readable medium including any conventional memory device, to perform any of the methods described herein, alone or in combination. The memory device can include any conventional permanent and/or temporary memory circuits or combination thereof, a non-exhaustive list of which includes Random Access Memory (RAM), Read Only Memory (ROM), Compact Disks (CD), Digital Versatile Disk (DVD), and magnetic tape.

An example embodiment of the present invention is directed to a hardware computer-readable medium, e.g., as described above, having stored thereon instructions executable by a processor to perform the methods described herein.

An example embodiment of the present invention is directed to a method, e.g., of a hardware component or machine, of transmitting instructions executable by a processor to perform the methods described herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 is a flowchart that illustrates a method for generating a VOA estimation model using a machine learning system, according to an example embodiment of the present invention.

FIGS. 2A-2B are block diagrams that illustrate a data flow into and out of a VOA estimation model, according to example embodiments of the present invention.

FIG. 3 is a flowchart that illustrates a method for using a VOA estimation model, according to an example embodiment of the present invention.

DETAILED DESCRIPTION

Figure 4:
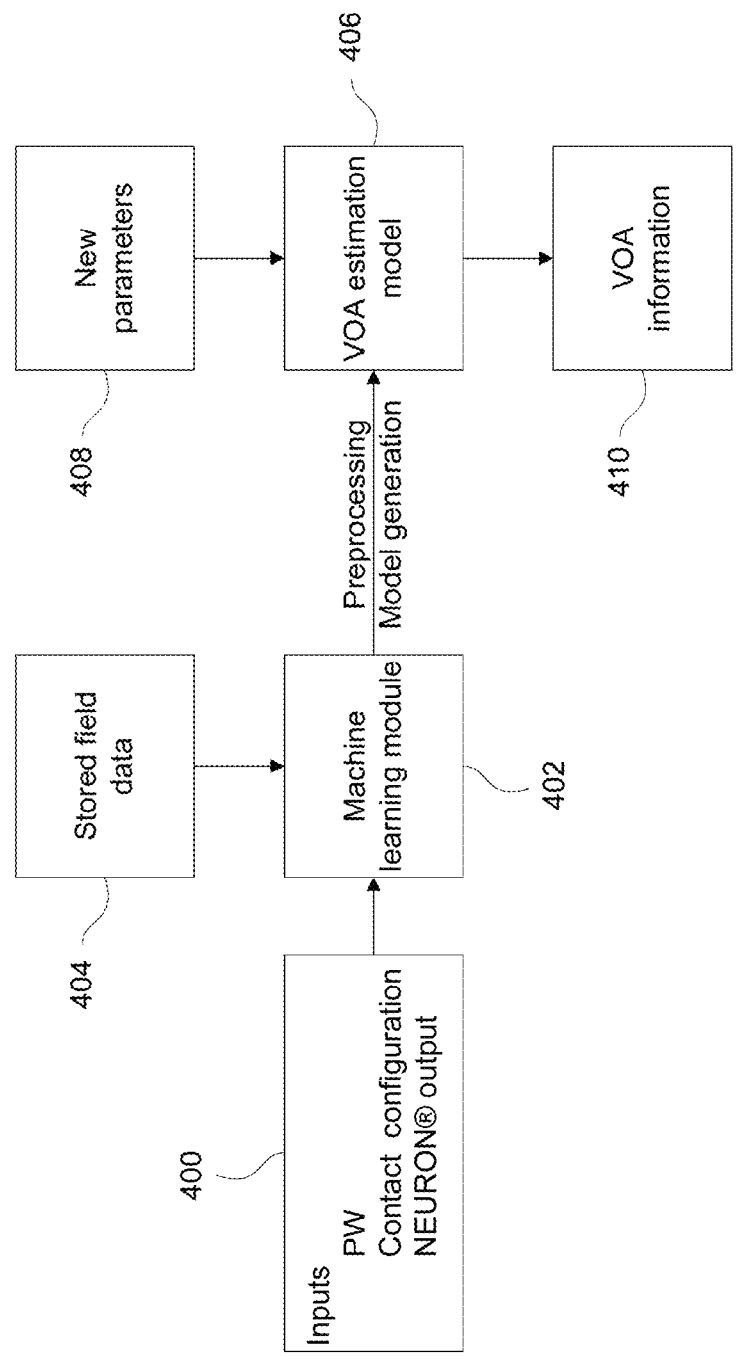
FIG. 4 is a diagram illustrating a data flow for generation and use of a VOA estimation model, according to an example embodiment of the present invention.

Example embodiments of the present invention relate to the automatic generation of a VOA estimation model, which receives input related to electromagnetic fields, e.g., voltage, current, magnetic flux, derivatives such as AF, etc., taken along spatial positions corresponding to test neural elements positioned at anatomical points surrounding an implanted stimulation producing leadwire, and, based on the input, classifies the anatomical points, as represented by the test neural element, as either activated or not activated. The test neural element can be selected from various types of neural elements including, for example, an axon, a dendrite, general fibers, a cell body, cell bodies with processes, a glial cell, etc. The definition of active and not active is also selectable. For example, any one of many neural events can be selected as an activation of the selected neural element. An example neural event is the firing of a neuron. For example, in an example embodiment, a neuron is used as the test neural element, the considered spatial positions taken along the neural element are the nodes of Ranviér, the data taken at each node of Ranviér is a voltage and/or AF value, and the neural event is the firing of the neuron, such that an anatomical point is considered active if it is determined that the test neuron plotted at the anatomical point fires considering the present stimulation settings of the leadwire and the voltage and/or AF values at the nodes of Ranviér of the plotted test neuron. However, in other example embodiments, other neural events can be considered for the activated/non-activated classification. For example, in the case of use of a glial cell as the test neural element, a simulation could be used to determine whether the cell is activated in a therapeutic manner which is the relevant neural event, e.g., cellular release of a neurotransmitter or ion. The combination of activated anatomical points classified as activated forms the VOA.

According to an example embodiment of the present invention, a method, as shown in FIG. 1, for generating an estimation model that outputs a VOA (or isosurface encompassing the VOA) includes, at step 100, inputting into a computationally expensive system a plurality of sets of information concerning a stimulation set-up. The system can include, for example, a non-linear neural element model, for example, that includes numerical integration. It can entail, for example, two or more interacting differential equations. It can be deterministic or probabilistic. Input to the computationally expensive system can include voltage or another parameter derived from voltage, e.g., electric field (EF) or activating function (AF), at several positions of a neural element.

An example of such a computationally expensive system is one that implements the software NEURON®. See Carnevale, N. T. et al., "The NEURON Book," Cambridge, UK: Cambridge University Press (2006). Another computationally expensive system can be used, but the description below of example embodiments will refer to NEURON®. The set of information can include information concerning the leadwire and its settings and/or electric field data in an anatomical region in which the leadwire is implanted. Different information sets can concern different leadwires, different stimulation settings, and/or different patients.

The computationally expensive system can then output membrane voltage over time, including action potentials or neural firing. For example, at step 102, for each set of information, respectively, NEURON® outputs an estimated region about the leadwire considered to be activated. To do so, NEURON® can determine the activation thresholds for a plurality of plotted neural elements given the electric field data. Those anatomical positions whose calculated activation thresholds are met by the present stimulation settings are considered to be activated. It is noted that synaptic inputs might also be used as input to NEURON® or might be part of that which is modeled by NEURON®.

While such computationally expensive systems provide what can be considered the gold standard for VOA output, they do not provide output quickly. Accordingly, the system and method of the present invention further provides a computationally inexpensive VOA estimation model based on data obtained from NEURON®. In this regard, at step 104, the input provided to NEURON®, including all of the sets of information, and all respective output of NEURON® are provided to a machine learning system. For example, a user can manually upload the NEURON® input and output to the machine learning system. Alternatively, a processor can execute a program that causes the processor to automatically input the data to the machine learning system, e.g., periodically or in response to a predetermined event, e.g., an output event by NEURON®.

In an example embodiment of the present invention, an Artificial Neural Network (ANN) is implemented as the machine learning system, e.g., for Pattern Recognition (PR) implementing Supervised Learning with Back-Propagation of Errors. For example, for supervised learning, it is possible for a human to input a base rule to the machine learning system, which then uses the input data from NEURON® to modify or build upon the rule. In other example embodiments, other machine learning/statistical classification techniques can be implemented. A non-exhaustive list of other example machine learning systems includes a decision tree analysis system, an association rules system, a genetic algorithms system, and a support vector machine (SVM) system.

The machine learning system can provide, for example, any one of or any combination of classification, clustering, function approximation, and/or prediction applications, can provide static (feedforward) or dynamic (feedback) connection types, can include a single layer, multilayer, recurrent, or self-organized topology, and can be implemented with a supervised or unsupervised learning method. For example, scaled conjugate gradient is one example supervised learning algorithm which can be implemented for training an ANN used as the machine learning system, but other training algorithms can be used. Various performance evaluation criteria can be alternatively used for a cost function of the machine learning system, e.g., mean square error. Any suitably appropriate machine learning can be used.

At step 106, the machine learning system configures a VOA estimation model, which can include, for example, a set of equations. The equations can, for example, manipulate numbers in the form of any one or more of scalars, vectors, matrices, etc., for example as weights and/or thresholds, etc.

For example, the machine learning system, in response to initial data from NEURON®, generates the model, and, in response to subsequent updated information from NEURON®, modifies the previously generated model to fit the new data. For example, subsequent to (or simultaneously with) the initial performance of step 106 by the machine learning system, steps 101 and 102 can be re-performed on new data, e.g., new leadwire setup or parameter data, and step 104 can be re-performed to provide the new data to the machine learning system, which accordingly updates, to the extent necessary, the previously generated VOA estimation model.

The model generated and/or updated at step 106 is less computationally expensive than NEURON®. For example, while NEURON® includes differential equations, the VOA estimation model, in an example embodiment, includes only linear equations. Further, while NEURON® analyzes the electric field over time and bases its activation determinations on such analyses, the VOA estimation model does not use as input a plurality of sets of values of the electric field, each set corresponding to a respective point in time (although time can still be a an indirect factor, for example, with input of stimulation timing paramers). Additionally, while NEURON® accepts a large amount of data as input parameters, the VOA estimation model, in an example embodiment, accepts fewer input parameters. For example, the VOA estimation model, in an example embodiment, is configured to receive as total electric field input two values of different data types or two or more values of the same type at a plurality of positions for each considered neural element. In yet another alternative example embodiment, the VOA estimation model is configured to receive as the electric field data two or more values for each of a plurality of data types, e.g., voltage values and AF values, at each of a plurality of positions for each considered neural element. Additional input can include certain stimulation settings, e.g., pulse width and/or current amplitude, for use to measure against the activation thresholds at the various anatomical points surrounding the leadwire. In an example embodiment, the VOA estimation model is configured to output a VOA (or corresponding isosurface) based on the input. However, as described below in connection with FIG. 2B, in an alternative example embodiment, the VOA estimation model does not perform the steps of determining activation status of the anatomical points or generating the visual VOA, but rather only determines the activation thresholds at the anatomical points (or a given neural element). According to this alternative example embodiment, the settings information used for measuring against the thresholds need not be input to the VOA estimation model. According to still further alternative example embodiments, although not shown in FIG. 2B, one or more of the settings, e.g., pulse width, are also used as input to the VOA estimation model even for the embodiments in which the VOA estimation model does not determine the activation status of anatomical points, where the determinations of the thresholds are also dependent on one or more presently set settings (but some of the settings, e.g., amplitude, would not be used).

In an example embodiment, while a single test neural element is selected for plotting at the relevant anatomical locations for the input to the VOA estimation model, a large number of different test neural elements with a variety of AF profiles with a variety of AF profiles along their lengths can be simulated in NEURON® to determine their activation status. These different data sets, including the different test neural elements along with the output of NEURON® can be provided to the machine learning system which generates the VOA estimation model configured for assuming the plotting of a selected single test neural element.

At step 108, new stimulation set-up information, e.g., corresponding to a different set-up than those previously considered by NEURON®, but which may be, for example, of a limited type for which the VOA estimation model is configured, is input into the VOA estimation model. (Alternatively, both NEURON® and the VOA estimation model operate on the same input data, but with less computationally expensive calculations being performed by the VOA estimation model than by NEURON®.) For example, the input can be provided to the machine learning system, which, in turn, inputs it into the VOA estimation model. At step 110, the VOA estimation model outputs a VOA based on the input.

At step 112, the input provided to the VOA estimation model is provided to NEURON®. In an example embodiment, an expanded version of the input is provided to NEURON®. For example, limited information as described above concerning the leadwire set-up is provided to the VOA estimation model, and that information and additional information, e.g., specifying the leadwire type, is provided to NEURON®. At step 114, NEURON® outputs an estimated activated region based on the new input.

At step 116, the machine learning system compares the VOA produced by the VOA estimation model and the activated region produced by NEURON®. If they are the same, the VOA estimation model can be considered complete, and the process can end (except that the VOA estimation model can continue to be updated with continued performance of steps 100-104). In an example embodiment, the process ends only if steps 108-116 are performed with a predetermined number or percentage of comparisons indicating consistency between NEURON® and the VOA estimation model. If the comparison indicates an inconsistency between the output of NEURON® and the VOA estimation model for one or more, e.g., a predetermined number or percentage of, leadwire set-ups, the method returns to step 106 for the machine learning system to update the VOA estimation model based on the new NEURON® data. For example, according to an example embodiment, the machine learning system must receive a predetermined amount of NEURON® data from which to learn and should demonstrate that it can mimic the NEURON® output.

The generated VOA estimation model can then be used, for any arbitrary stimulation settings on any arbitrary lead, to classify each of a plurality of anatomical positions as activated or non-activated, e.g., based on AF values at a plurality of nodes along the test neural element plotted at the respective anatomical position. For example, FIG. 2A is a data flow diagram that shows the input of field data, e.g., AF values, and present stimulation parameters to the VOA estimation model generated by the machine learning system. The VOA estimation model is then configured to, based on the field data and present stimulation settings, e.g., the current amplitude of the electrodes, determine for each of a plurality of neural elements whether the respective neural element is activated. In an example embodiment, the system is further configured to generate as the VOA a visual representation of an area including a combination of the neural elements classified as having been activated. In an alternative example embodiment, the field data input itself provides a sufficient basis for the VOA estimation model to determine for each of the neural elements, whether the neural element is activated. For example an AF profile along a neural element can be indicative of the electrode power and its effect on the neural element, the AF profile thereby being used to determine whether the neural element is activated.

It is noted that what is considered to constitute the VOA estimation model generated by the machine learning system can include more or less of the described modules. For example, in an example embodiment, the module for generating the visual display can be considered to be encompassed by the VOA estimation model itself. Similarly, as shown in FIG. 2B, the VOA estimation model can be considered to include those modules that receive as input only the field data and that outputs only the activation threshold at each considered anatomical point (or that receive as input both the field data and a set of stimulation parameters, but outputs only the activation at each considered anatomical point). A separate module can then obtain the threshold information from the VOA estimation model and the present stimulation parameters, output an activated/non-activated status for each anatomical point based on the respective thresholds and the present stimulation parameters, and, based on such output, produce the visual representation of the VOA. According to this example embodiment, what is compared at step 116 can be the respectively produced collections of NEURON® and the VOA estimation model of activation thresholds for the respective anatomical points.

As noted above, example embodiments provide that activation thresholds are determined by the VOA estimation model on a neural element by neural element basis, and therefore whether or not a particular anatomical point is classified as activated depends on whether the present stimulation parameters meet the respective activation threshold determined for the neural element plotted at the respective anatomical point.

FIG. 3 illustrates a method for using the VOA estimation model generated according to the method illustrated in FIG. 1. At step 300, the system selects a plurality of points in a three dimensional space about an implanted leadwire. For example, the system can be configured to select all points within a predetermined distance from the electrode. At step 302, the system plots a predetermined virtual neural element at each of the selected points. For example, an axon can be used as the virtual neural element, and it can be plotted for each of the selected points such that the axon passes through the respective point of interest. (Alternatively, other neural elements can be used instead, as noted above. For example, the neural element can be a cell body, dendrite, glial cell, or a cell body with attached processes.) In the case of an axon, the axon can lie on a straight line, or can possess a curve along one, two, or three dimensions. The path that the axon takes through space is referred to as its trajectory. This trajectory can be determined by a set of rules (e.g., the trajectory is to be in the form of a straight line parallel to a plane tangent to the leadwire at a point on the lead surface which is closest to the point of interest), by universal data which is saved to the final implemented product (e.g., exemplary camera lucida tracings) so that the trajectory is set in the same way for all patients, or from patient-specific data (e.g., tractography determined by DTI image processing) so that the trajectory is differently set for different patients. For example, DTI MRI can include information that would allow models of fiber trajectories to be generates, as is convention in academic analyses. In a further example embodiment, the trajectories are similarly set for patients of a same defined patient category but different for patients of different defined patient categories. The trajectories can be determined by rules, imaging data, or a combination thereof.

At step 304, the system maps field parameters to a point or multiple points along each of the plotted neural elements. For example, in the case of use of an axon as the virtual neural element, points are typically chosen at the centers of compartments which are representative of anatomic elements of the fiber. As an example implementation, 21 points located to correspond to 21 nodes of Ranviér may be chosen at which the field parameters are identified. A non-exhaustive list of example field parameters to be identified at one or more locations of the virtual neural element includes:

scalar potential field;
second central difference of the potential field (Activating Function (AF));
electric tensor field or magnitude thereof;
temperature; and
current tensor field or magnitude thereof.

At step 306, the system inputs the plotted neural element data and field data, e.g., as a vector, to the VOA estimation model, which outputs VOA data as a visual representation of a volume including the neural elements classified as activated, a collection of activation classifications for the plurality of plotted neural elements, or a collection of activation thresholds for the plurality of plotted neural elements. According to the latter two example embodiments (in which the VOA estimation model does not itself generate the visual representation), another module can process the output of the VOA estimation model to generate the visual representation as the VOA.

According to an alternative example embodiment, a generic model of plotted neural elements at preset locations is used, so that steps 300 and 302 need not be repeated for each use of the model. Instead, according to this alternative example embodiment, for determining an activation threshold and/or an estimated volume of activation, current field parameters are plotted at the plotted neural elements of the generic model.

In an example embodiment of the present invention, the VOA estimation model can essentially be a black box, in that a programmer need not define or even know the equations forming the VOA estimation model. Instead, the machine learning produces as the VOA estimation model a set of equations, which can vary over time as input to the machine learning system is updated.

In an example embodiment, the machine learning system steps can be performed at a manufacturer of the program. Alternatively, the described learning steps can be performed locally at a Clinician Programmer station operated by a clinician, so that it continuously updates based on information provided by the clinician's use over time. The latter embodiment can result in a scenario where different models are generated for different clinicians based on the different input obtained over time at the different Clinician Programmer stations for the respective machine learning operations.

In an example embodiment of the present invention the machine learning is used to generate a plurality of VOA estimation models, each corresponding to a respective category of stimulation and/or leadwire arrangement parameters and/or patient anatomical structures. Such VOA estimation models can be more accurate for generating the estimated VOAs for particular corresponding settings or characteristics, than a single more general VOA estimation model, for example, because the machine learning is more fine tuned to generate sets of rules appropriate for respective kinds of data.

For example, a separate VOA estimation model can be generated for each of a plurality of pulse widths, pulse width ranges, and/or pulse width combinations (e.g., where a stimulation program includes cycling through different pulse widths). For example, the machine learning system can divide the data received from NEURON® into subsets corresponding to the respective pulse width categories, and separately configure the respective VOA estimation models at steps 106-116. Subsequently, for example, in response to receipt of input, e.g., from a clinician, of stimulation parameters, the system selects one of the previously generated VOA estimation models depending on the pulse width setting of the received input. For example, the system selects the VOA estimation model corresponding to the pulse width setting that matches that of the received input. In an example embodiment, if none of the generated VOA estimation models correspond to a parameter (e.g., the pulse width in the embodiment in which separate VOA estimation models are generated for different pulse widths) that matches precisely with that of the input, the system selects the that of the VOA estimation models which corresponds to a parameter that most closely, compared to the parameters to which the others of the VOA estimation models correspond, matches the relevant parameter of the received input. The selected VOA estimation model is then used to ultimately output a visual representation of a VOA corresponding to the parameters of the received input. It is noted that the parameters for which the visual rendering is output need not be directly input by a user. For example, the stimulation parameters can be suggested by the system itself, for example as discussed in the '330, '312, '340, '343, and '314 applications.

Additional or alternative criteria can be used as categories for which corresponding VOA estimation models are generated. For example, a characteristic of the field data of the data sets for which NEURON® generates the activated region information in step 102 can be used to categorize the data, for which categories respective VOA estimation models are generated. For example, in an example embodiment, the machine learning system separates the data according AF profiles, such that a respective VOA estimation model is generated for those data sets whose electric field data represents a cathodically shaped AF profile (positive maximal excursion), those data sets whose electric field data represents an anodically shaped AF field (negative maximal excursion), and those data sets whose electric field data represents a mixed AF field (approximately equal maximal positive and negative excursions). An advantage to categorizing by AF profile is that, while a human might intuitively recognize characteristics of overall AF shape, the machine learning system analyzes the data as a plurality of discrete values without necessarily recognizing the significance of certain overall shapes in the analysis. The separation of the data by overall AF shape causes the machine learning system to learn rules for a corresponding shape without being affected by behavior associated with other shapes, whose behavior can differ on account of the different AF shape. For example, in the case of cathodically shaped AF profiles, there is a mid-point peak value that causes activation, while, in the case of anodically shaped AF profiles, two points adjacent to such a mid-point value cause the activation.

In an example embodiment of the present invention, prior to the machine learning system processing of the data received from NEURON®, the system performs a preprocessing of the data, for example, to provide for some a consistency in a selected characteristic between the input data. Such consistency can help the machine learning system recognize rules. For example, in the case of a cathodically shaped AF profile, a peak point causes activation, and therefore the peak point is a significant feature to be analyzed by the machine learning system. Accordingly, in an example embodiment, prior to analysis by the machine learning system for determining rules of the VOA estimation model, preprocessing is performed on raw electric field data to shift the peak value to a predetermined location with respect to its surrounding data, e.g., to be positioned at data position 1 of 10 or some other predetermined position. Thus, in an example embodiment, the data from the neural element is shifted in its vector formation (e.g., $AF_5$ set to $AF_1$) such that the expected location of some relevant portion (e.g., peak) in the data is passed at a predetermined location within the input vector. This scheme may be termed shift invariance, as it accounts for shift in the data along the dimension of the input vector itself.

Other preprocessing can include scaling the input data and/or performing a pattern-matching of the data. Other preprocessing can also additionally or alternatively be performed.

FIG. 4 shows an example data flow beginning with input to the machine learning system, continuing with generation of a VOA estimation model, and concluding with output by the VOA estimation model of VOA information. Inputs 400 are provided to a machine learning system 402. Example inputs include pulse width information, contact configuration information, and NEURON® output for the corresponding pulse width and contact configuration information. The machine learning system 402 can access a stored field data table 404 to obtain voltage field data corresponding to the contact configuration information. For example, the table 404 can include specifications of respective voltage fields for each of a plurality of contact configurations. Based on the NEURON® output and the obtained voltage field, the machine learning module generates the VOA estimation model 406. In an example embodiment, the pulse width information is used to generate multiple VOA estimation models 406 for respective pulse width categories. As described in detail above, the data can be additionally or alternatively divided by other categories, e.g., AF profile. The machine learning system 402 can perform preprocessing on the input 400 to determine the categorical classification of the data, in order to perform separate analyses for each of the categories, thereby yielding the different versions of the VOA estimation model 406. Other preprocessing can also be performed as described in detail above. Once the VOA estimation model 406 is generated, new stimulation parameters 408 can be input to the (appropriate version of the) VOA estimation model 406, which outputs based on such input VOA information 410, which can include activation thresholds of respective anatomical points, activation statuses of respective anatomical points, and/or a visual VOA representation or isosurface.

In the illustrated example, the machine learning module 402 generates different VOA estimation models 406 for different pulse widths. For example, a separate respective set of weights, bias values, and ANN transfer functions can be defined for each categorized pulse width.

The contact configuration information used to select the appropriate electric field map can identify a distribution of current on the contacts of the leadwire as well as the casing, e.g., in the form of raw delimited current values, for example, $-2,0,1,0,0,0,0,0,1mA$, where the current on the casing is underlined, or as a fractionalized percentage, e.g., $1,0,-0.5,0,0,0,0,0,\underline{0.5}$.

In an example embodiment, the stored field data table 404 is a single table of voltages due to unit current (+1) for each contact. For each active contact, the corresponding normalized potential values are multiplied by the value of the current on the contact, and then the sum is taken of the scaled potential values. For example, a respective potential field in space can be stored for each contact at unit current. For any given point, the potential value at that point is determined for each one of the contacts by multiplying the stored value by the input current value given for that contact. All of the products for that given point are then summed to produce the field potential value at that point.

Figure 5:
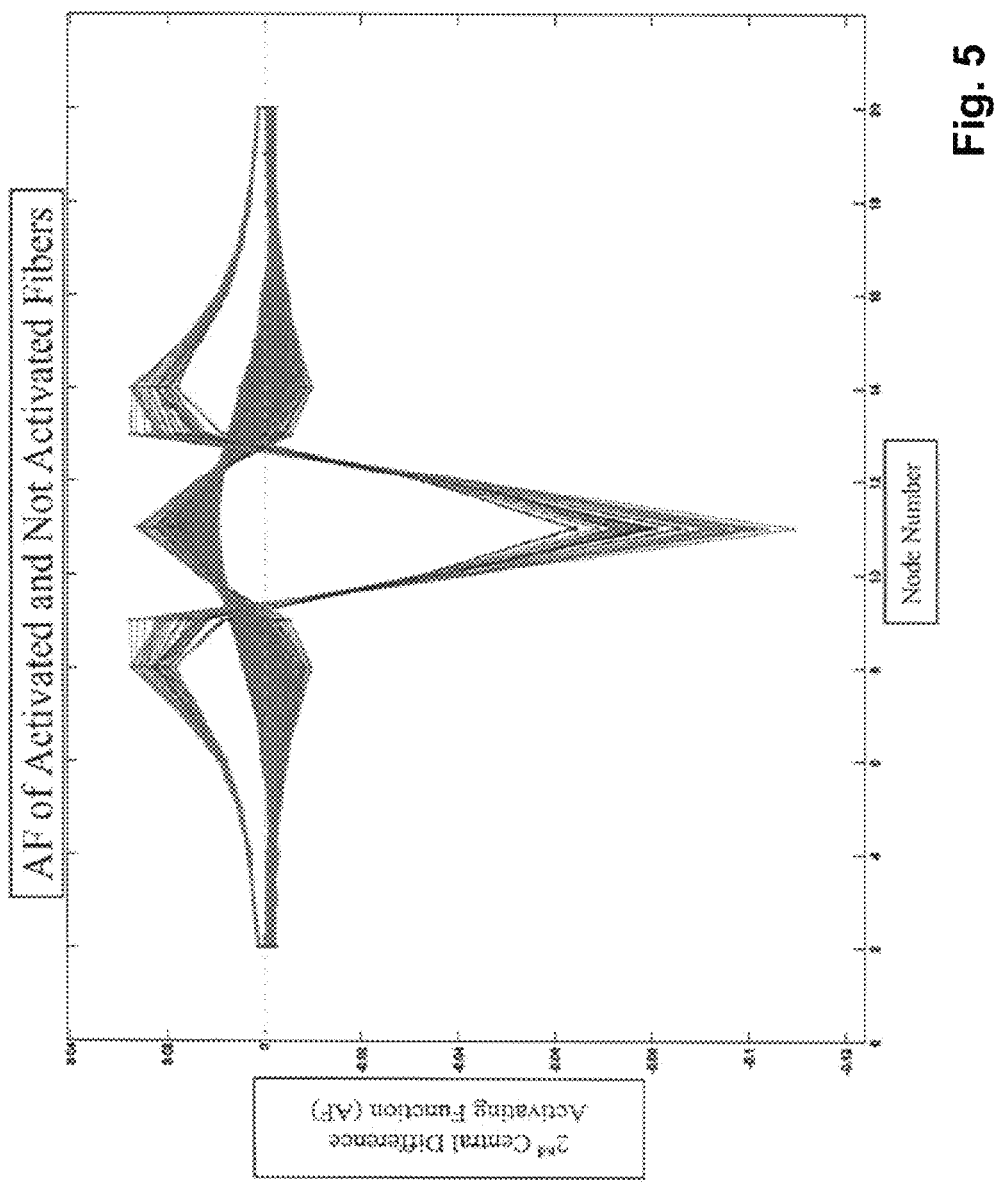
FIG. 5 is a graph of plotted data that can be input to a machine learning system for generating a VOA estimation model, according to an example embodiment of the present invention.

FIG. 5 is a graph that shows an example of input that can be provided to the machine learning system on which basis the machine learning system generates the rules of the VOA estimation model. The graph plots a plurality of AF profiles, each profile including a plurality of AF values at respective ones of 19 nodes of Ranviér of an axon, where the blue profiles correspond to those for which NEURON® had calculated an activated status for the axon and the red profiles correspond to those for which NEURON® had calculated a non-activated status for the axon. In an example embodiment of the present invention, based on the input of the AF profiles and the corresponding NEURON® output, the machine learning system generates the VOA estimation model, which, when presented with a new AF profile, determines whether the axon to which the input AF profile corresponds is activated.

In a test case, an ANN for pattern recognition and binary statistical classification was used as a machine learning system to generate a VOA estimation model that was used to classify 45,360 axons spaced on a regular grid with 0.1 mm spatial resolution in the radial and z directions. The ANN was trained to classify axons with cathodically shaped AF profiles and correctly classified over 99% of the axons, with, by comparison to NEURON® output, a total of only 114 misclassified axons across 48 contact configurations for an average of 2.375 misclassified axons per contact configuration. In view of the above-noted resolution, any misclassification of axons on the boundary between activated and non-activated axons represented a distance error of at most 0.1414 mm. Of the 45,360 axons, the VOA estimation model resulted in 35,517 (78.3%) true negatives (correctly determined non-activated statuses), 9,729 (21.4%) true positives (correctly determined activated statuses), 47 (0.1%) false negatives (incorrectly determined non-activated statuses), and 67 (0.1%) false positives (incorrectly determined activated statuses).

The above description is intended to be illustrative, and not restrictive. Those skilled in the art can appreciate from the foregoing description that the present invention may be implemented in a variety of forms, and that the various embodiments may be implemented alone or in combination. Therefore, while the embodiments of the present invention have been described in connection with particular examples thereof, the true scope of the embodiments and/or methods of the present invention should not be so limited since other modifications will become apparent to the skilled practitioner upon a study of the drawings, specification, and the following claims.

What is claimed is:

1. A system for estimating a volume of activation using a set of electrical stimulation settings, the system comprising:
a processor configured to:
receive electric field data and the set of electrical stimulation settings for use with a non-cylindrically symmetrical implanted leadwire;
apply the electric field data and the set of electrical stimulation settings to a volume of activation estimation model to determine a value for each of one of more locations for each of a plurality of neural elements, wherein the volume of activation estimation model either 1) does not use as input a plurality of sets of values of an electrical field at different points in time, 2) includes only linear equations generated based on observed functioning of a model that uses differential equations, or 3) does not use more than one differential equation;
output an indication of an estimated volume of activation based on the values for each of the one or more locations for each of the neural elements; and
initiate a signal to convey the set of electrical stimulation settings to an implanted pulse generator to transmit signals via a leadwire for stimulation of patient tissue according to the set of electrical stimulation settings.

2. The system of claim 1, wherein the volume of activation estimation model is generated based on observed functioning of the model that uses differential equations, wherein the observed functioning comprises using machine learning to generate the volume of activation estimation model.

3. The system of claim 2, wherein the machine learning comprises decision tree analysis learning.

4. The system of claim 2, wherein the machine learning implements at least one of Artificial Neural Network (ANN), association rules, genetic algorithms, or support vector machines.

5. The system of claim 4, wherein the ANN learning implements pattern recognition with back-propagation of errors.

6. The system of claim 1, wherein the neural elements are axons.

7. The system of claim 6, wherein the axons are all copies of a same model axon, each plotted at a respective point relative to the leadwire.

8. The system of claim 1, wherein the electric field data comprises, for each of the plurality of neural elements, a value of an activating function at one or more locations along the neural element and the activating function is a second difference activating function.

9. The system of claim 1, wherein the one or more locations are nodes of Ranviér of the respective neural element.

10. The system of claim 1, wherein the electric field data comprises, for each of the plurality of neural elements, a value of an activating function at one or more locations along the neural element and the activating function comprises an activating function profile at a plurality of locations along the neural element.

11. The system of claim 1, wherein the volume of activation estimation model comprises a plurality of volume of activation estimation models, each of the volume of activation estimation models corresponding to a different pulse width.

12. A non-transitory computer-readable medium having instructions stored thereon and executable by a processor, the instructions comprising:
receiving electric field data and the set of electrical stimulation settings for use with a non-cylindrically symmetrical implanted leadwire;
applying the electric field data and the set of electrical stimulation settings to a volume of activation estimation model to determine a value for each of one of more locations for each of a plurality of neural elements, wherein the volume of activation estimation model either 1) does not use as input a plurality of sets of values of an electrical field at different points in time, 2) includes only linear equations generated based on observed functioning of a model that uses differential equations, or 3) does not use more than one differential equation;
outputting an indication of an estimated volume of activation based on the values for each of the one or more locations for each of the neural elements; and
initiating a signal to convey the set of electrical stimulation settings to an implanted pulse generator to transmit signals via a leadwire for stimulation of patient tissue according to the set of electrical stimulation settings.

13. The non-transitory computer-readable medium of claim 12, wherein the volume of activation estimation model is generated based on observed functioning of the model that uses differential equations, wherein the observed functioning comprises using machine learning to generate the volume of activation estimation model.

14. The non-transitory computer-readable medium of claim 13, wherein the machine learning comprises decision tree analysis learning.

15. The non-transitory computer-readable medium of claim 13, wherein the machine learning implements at least one of Artificial Neural Network (ANN), association rules, genetic algorithms, or support vector machines.

16. The non-transitory computer-readable medium of claim 12, wherein the neural elements are axons.

17. The non-transitory computer-readable medium of claim 16, wherein the axons are all copies of a same model axon, each plotted at a respective point relative to the leadwire.

18. The non-transitory computer-readable medium of claim 12, wherein the electric field data comprises, for each of the plurality of neural elements, a value of an activating function at one or more locations along the neural element and the activating function is a second difference activating function.

19. The non-transitory computer-readable medium of claim 12, wherein the one or more locations are nodes of Ranviér of the respective neural element.

20. The non-transitory computer-readable medium of claim 12, wherein the volume of activation estimation model comprises a plurality of volume of activation estimation models, each of the volume of activation estimation models corresponding to a different pulse width.

* * * * *